(12) United States Patent
McDonnell et al.

(10) Patent No.: US 12,150,998 B2
(45) Date of Patent: Nov. 26, 2024

(54) BICYCLIC PEPTIDE LIGANDS SPECIFIC FOR P-SELECTIN

(71) Applicant: BicycleTx Limited, Cambridge (GB)

(72) Inventors: Kevin McDonnell, Lexington, MA (US); Gemma Mudd, Cambridge (GB); Michael Skynner, Cambridge (GB); Sophie Watcham, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 17/659,934

(22) Filed: Apr. 20, 2022

(65) Prior Publication Data

US 2022/0339289 A1 Oct. 27, 2022

Related U.S. Application Data

(60) Provisional application No. 63/177,185, filed on Apr. 20, 2021.

(51) Int. Cl.
| | |
|---|---|
| *C07K 7/00* | (2006.01) |
| *A61K 47/64* | (2017.01) |
| *C07K 7/06* | (2006.01) |
| *C07K 14/745* | (2006.01) |

(52) U.S. Cl.
CPC ............... *A61K 47/64* (2017.08); *C07K 7/06* (2013.01); *C07K 14/745* (2013.01); *C07K 2319/30* (2013.01)

(58) Field of Classification Search
CPC ........ A61K 47/64; C07K 7/06; C07K 14/745; C07K 2319/30
See application file for complete search history.

(56) References Cited

U.S. PATENT DOCUMENTS

| | | | | |
|---|---|---|---|---|
| 2016/0128958 A1* | 5/2016 | Silverman | ............ | A61K 31/196 435/375 |
| 2019/0263866 A1* | 8/2019 | Chen | ...................... | C07K 17/02 |

FOREIGN PATENT DOCUMENTS

| | | |
|---|---|---|
| WO | 03020753 A1 | 3/2003 |
| WO | 2004105783 A1 | 12/2004 |
| WO | WO-2009098450 A2 | 8/2009 |
| WO | 2018197509 A1 | 11/2018 |
| WO | 2018197893 A1 | 11/2018 |
| WO | 2019162682 A1 | 8/2019 |
| WO | 2020084305 A1 | 4/2020 |
| WO | 2022223969 A1 | 10/2022 |

OTHER PUBLICATIONS

Chantal et al. (2003). vol. 278, No. 12, Issue of Mar. 21, pp. 10201-10207.*
Cherney et al., "Macrocyclic Amino Carboxylates as Selective MMP-8 Inhibitors," J. Med. Chem., 1998, vol. 41, pp. 1749-1751.
Driggers et al., "The Exploration of Macrocycles for Drug Discovery—an Underexploited Structural Class," Nat Rev Drug Discov, 2008, vol. 7(7), pp. 608-624.
Heinis et al., "Phage-encoded combinatorial chemical libraries based on bicyclic peptides", Nature Chemical Biology, vol. 5, No. 7, May 31, 2009; pp. 502-507, XP002588840.
Kemp and McNamara, "Conformationally Restricted Cyclic Nonapeptides Derived from L-Cysteine and LL-3-Amino-2-Piperidone-6-Carboxylic Acid (LL-Acp), a Potent β-Turn-Inducing Dipeptide Analogue," J. Org. Chem, 1985, vol. 50, pp. 5834-5838.
Nair et al.,, "Mimicry of Native Peptide Antigens by the Corresponding Retro-Inverso Analogs is Dependent on Their Intrinsic Structure and Interaction Propensities," J Immunol, 2003, vol. 170(3), pp. 1362-1373.
Timmerman et al., "Rapid and Quantitative Cyclization of Multiple Peptide Loops onto Synthetic Scaffolds for Structural Mimicry of Protein Surfaces," ChemBioChem, 2005, vol. 6, pp. 821-824.
Xiong et al., "Crystal Structure of the Extracellular Segment of Integrin αVβ3 in Complex with an Arg-Gly-Asp Ligand," Science, 2002, vol. 296 (5565), pp. 151-155.
Zhao et al., "Structural Basis of Specificity of a Peptidyl Urokinase Inhibitor, Upain-1," J Struct Biol, 2007, vol. 160(1), pp. 1-10.
Wu et al., "Structure of the CXCR4 Chemokine GPCR with Small-Molecule and Cyclic Peptide Antagonists," Science. 2020:330;1066-1071.
Heinis et al., "Peptide Ligands Stabilized by Small Molecules," Angew. Chem. Int. Ed. 2014:53;1602-1606.
Deyle et al., "Phage Selection of Cyclic Peptides for Application in Research and Drug Development", Accounts of Chemical Research, 2017, 50(8):1866-1874.
Kale et al., "Cyclization of peptides with two chemical bridges affords large scaffold diversities", Nature Chemistry, 2018, 10(7):715-723.

(Continued)

*Primary Examiner* — Jeanette M Lieb
(74) *Attorney, Agent, or Firm* — Dechert LLP; Andrea L.C. Reid; Gang Wang

(57) ABSTRACT

The present invention relates to polypeptides which are covalently bound to molecular scaffolds such that two or more peptide loops are subtended between attachment points to the scaffold. In particular, the invention describes peptides which bind to P-selectin. The invention also relates to multimeric binding complexes of polypeptides which are covalently bound to molecular scaffolds such that two or more peptide loops are subtended between attachment points to the scaffold that are binders of P-selectin. The invention also includes drug conjugates comprising said peptides and complexes, conjugated to one or more effector and/or functional groups, to pharmaceutical compositions comprising said peptide ligands, complexes and drug conjugates and the use of said peptide ligands and drug conjugates in preventing, suppressing or treating a disease or disorder mediated by a cell adhesion molecule, such as P-selectin, including vaso-occlusive crisis and sickle cell disease-related conditions, cancer, or COVID-19.

23 Claims, 1 Drawing Sheet

Specification includes a Sequence Listing.

(56) References Cited

OTHER PUBLICATIONS

Molenaar et al., "Specific inhibition of P-selectin-mediated cell adhesion by phage display-derived peptide antagonists", Blood, Nov. 15, 2002, 100(10):3570-3577.
International Preliminary Report on Patentability received for PCT Patent Application No. PCT/GB2022/050995, completed on Jun. 21, 2023, 7 pages.
International Search Report and Written Opinion received for PCT Patent Application No. PCT/GB2022/050995, mailed on Sep. 2, 2022, 13 pages.

* cited by examiner

SEQUENCE LISTING

<160> NUMBER OF SEQ ID NOS: 6

<210> SEQ ID NO 1
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is D or Y
<220> FEATURE:
<221> NAME/KEY: Xaa
<222> LOCATION: (3)..(3)
<223> OTHER INFORMATION: Xaa is A or M
<220> FEATURE:
<221> NAME/KEY: Xaa
<222> LOCATION: (4)..(4)
<223> OTHER INFORMATION: Xaa is D or E
<220> FEATURE:
<221> NAME/KEY: Xaa
<222> LOCATION: (5)..(5)
<223> OTHER INFORMATION: Xaa is W, 1Nal or Trp(Me)
<220> FEATURE:
<221> NAME/KEY: Xaa
<222> LOCATION: (10)..(10)
<223> OTHER INFORMATION: Xaa is P or T
<220> FEATURE:
<221> NAME/KEY: Xaa
<222> LOCATION: (11)..(11)
<223> OTHER INFORMATION: Xaa is S or D
<220> FEATURE:
<221> NAME/KEY: Xaa
<222> LOCATION: (12)..(12)
<223> OTHER INFORMATION: Xaa is L or Y
<220> FEATURE:
<221> NAME/KEY: Xaa
<222> LOCATION: (13)..(13)
<223> OTHER INFORMATION: Xaa is P or G

<400> SEQUENCE: 1

Cys Xaa Xaa Xaa Xaa Cys Asp Val Thr Xaa Xaa Xaa Xaa Cys
1               5                   10

<210> SEQ ID NO 2
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is 1Nal

<400> SEQUENCE: 2

Cys Asp Ala Asp Xaa Cys Asp Val Pro Ser Leu Pro Cys
1               5                   10

<210> SEQ ID NO 3
<211> LENGTH: 13
<212> TYPE: PRT
<213> ORGANISM: Artificial
<220> FEATURE:
<223> OTHER INFORMATION: Synthetic Peptide

<400> SEQUENCE: 3

Cys Asp Ala Asp Trp Cys Asp Val Pro Ser Leu Pro Cys
1               5                   10

<210> SEQ ID NO 4

```
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is 1Nal

<400> SEQUENCE: 4

Cys Tyr Met Glu Xaa Cys Asp Val Thr Asp Tyr Gly Cys
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is Trp(Me)

<400> SEQUENCE: 5

Cys Tyr Met Glu Xaa Cys Asp Val Thr Asp Tyr Gly Cys
1               5                   10

<210> SEQ ID NO 6
<211> LENGTH: 13
<212> TYPE: PRT
<213> ORGANISM: Artificial
<220> FEATURE:
<223> OTHER INFORMATION: Synthetic Peptide

<400> SEQUENCE: 6

Cys Tyr Met Glu Trp Cys Asp Val Thr Asp Tyr Gly Cys
1               5                   10
```

BICYCLIC PEPTIDE LIGANDS SPECIFIC FOR P-SELECTIN

CROSS-REFERENCE TO RELATED APPLICATIONS

The present application claims priority to U.S. Provisional Patent Application Ser. No. 63/177,185, filed Apr. 20, 2021, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Apr. 20, 2022, is named 392664-046US_190510_SL.txt and is 2,219 bytes in size.

FIELD OF THE INVENTION

The present invention relates to polypeptides which are covalently bound to molecular scaffolds such that two or more peptide loops are subtended between attachment points to the scaffold. In particular, the invention describes peptides which bind to P-selectin. The invention also relates to multimeric binding complexes of polypeptides which are covalently bound to molecular scaffolds such that two or more peptide loops are subtended between attachment points to the scaffold that are binders of P-selectin. The invention also includes drug conjugates comprising said peptides and complexes, conjugated to one or more effector and/or functional groups, to pharmaceutical compositions comprising said peptide ligands, complexes and drug conjugates and the use of said peptide ligands and drug conjugates in preventing, suppressing or treating a disease or disorder mediated by a cell adhesion molecule, such as P-selectin, including vaso-occlusive crisis and sickle cell disease-related conditions, cancer, or COVID-19.

BACKGROUND OF THE INVENTION

Cyclic peptides are able to bind with high affinity and specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat. Rev. Drug. Discov. 7(7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu et al. (2007), Science 330, 1066-71), a cyclic peptide with the Arg-Gly-Asp motif binding to integrin αVb3 (355 $Å^2$) (Xiong et al. (2002), Science 296(5565), 151-5) or the cyclic peptide inhibitor upain-1 binding to urokinase-type plasminogen activator (603 $Å^2$; Zhao et al. (2007), J. Struct. Biol. 160(1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J. Med. Chem. 41(11), 1749-51). The favourable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example 1,1',1"-(1,3,5-triazinane-1,3,5-triyl)triprop-2-en-1-one (TATA) (Heinis et al. (2014) Angewandte Chemie, International Edition 53(6) 1602-1606).

Phage display-based combinatorial approaches have been developed to generate and screen large libraries of bicyclic peptides to targets of interest (Heinis et al. (2009), Nat. Chem. Biol. 5(7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for P-selectin comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a multimeric binding complex which comprises at least two peptide ligands, wherein at least one peptide ligand is specific for P-selectin as defined herein and said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a yet further aspect of the invention, there is provided a drug conjugate comprising the peptide ligand or multimeric binding complex as defined herein, conjugated to one or more effector and/or functional groups.

According to a yet further aspect of the invention, there is provided a pharmaceutical composition comprising a peptide ligand, multimeric binding complex or drug conjugate as defined herein in combination with one or more pharmaceutically acceptable excipients.

According to a further aspect of the invention, there is provided a peptide ligand, multimeric binding complex, drug conjugate or pharmaceutical composition as defined herein for use in preventing, suppressing or treating a disease or disorder mediated by P-selectin.

DETAILED DESCRIPTION OF THE INVENTION

Peptide Ligands

Figure 1:
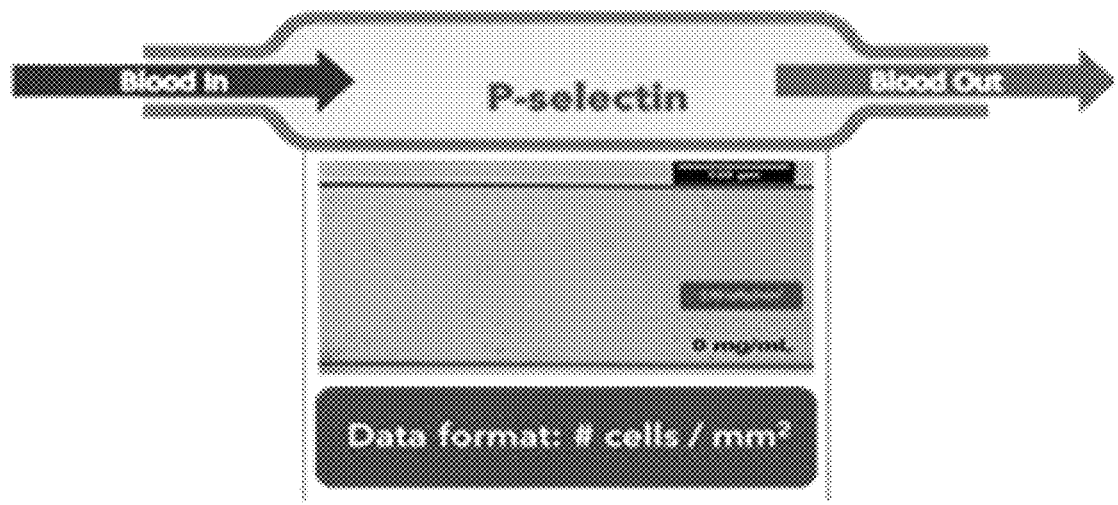
FIG. 1: Schematic representation of P-selectin flow adhesion assay.

According to a first aspect of the invention, there is provided a peptide ligand specific for P-selectin comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

In one embodiment, said reactive groups comprise cysteine residues.

In a further embodiment, said peptide ligand comprises the motif WCDV. The WCDV amino acid motif has previously been shown to confer binding of linear peptide ligands to P-selectin. However, the present inventors surprisingly found that the binding affinity of such a motif, and modified derivatives thereof is enhanced when incorporated within the bicyclic peptides as described herein. In a yet further embodiment, said peptide ligand comprises a modified derivative of the motif WCDV.

In a further embodiment, said loop sequences comprise 4 or 6 amino acids.

In one embodiment, said loop sequences comprise three cysteine residues separated by two loop sequences the first of which consists of 4 amino acids and the second of which consists of 6 amino acids.

In one embodiment, the peptide ligand comprises an amino acid sequence of:

(SEQ ID NO: 1)
$C_i$-X$_1$-X$_2$-X$_3$-X$_4$-$C_{ii}$-D-V-T-X$_5$-X$_6$-X$_7$-X$_8$-$C_{iii}$, wherein
X$_1$ represents D or Y;
X$_2$ represents A or M;
X$_3$ represents D or E;
X$_4$ represents W, 1Nal or Trp(Me);
X$_5$ represents P or T;
X$_6$ represents S or D;
X$_7$ represents L or Y;
X$_8$ represents P or G;
wherein 1Nal represents 1-naphthylalanine, Trp(Me) represents methyl-tryptophan and $C_i$, $C_{ii}$ and $C_{iii}$ represent first, second and third cysteine residues, respectively, or a modified derivative, or a pharmaceutically acceptable salt thereof.

In a further embodiment, X$_4$ represents W.

In a yet further embodiment, the peptide ligand of $C_i$-X$_1$-X$_2$-X$_3$-X$_4$-$C_{ii}$-D-V-T-X$_5$-X$_6$-X$_7$-X$_8$-$C_{iii}$ (SEQ ID NO: 1) comprises an amino acid sequence selected from:

(SEQ ID NO: 2)
$C_i$DAD[1Nal]$C_{ii}$DVPSLP$C_{iii}$;

(SEQ ID NO: 3)
$C_i$DADW$C_{ii}$DVPSLP$C_{iii}$;

(SEQ ID NO: 4)
$C_i$YME[1Nal]$C_{ii}$DVTDYG$C_{iii}$;

(SEQ ID NO: 5)
$C_i$YME[Trp(Me)]$C_{ii}$DVTDYG$C_{iii}$;
and (SEQ ID NO: 6)
$C_i$YMEW$C_{ii}$DVTDYG$C_{iii}$;

wherein $C_i$, $C_{ii}$ and $C_{iii}$ represent first, second and third cysteine residues, respectively, or a modified derivative, or a pharmaceutically acceptable salt thereof).

In a further embodiment, the peptide ligand comprises N- and/or C-terminal additions and is selected from:
A-(SEQ ID NO: 2)-A (herein referred to as BCY12027);
H$_2$N-A-(SEQ ID NO: 2)-A-[K(PYA)] (herein referred to as BCY12026);
A-(SEQ ID NO: 3)-A (herein referred to as BCY11648);
H$_2$N-A-(SEQ ID NO: 3)-A-[K(PYA)] (herein referred to as BCY12025);
Ac-A-(SEQ ID NO: 4)-A (herein referred to as BCY11279);
A-(SEQ ID NO: 4)-A-[K(PYA)] (herein referred to as BCY11890);
Ac-A-(SEQ ID NO: 5)-A (herein referred to as BCY11281);
Ac-(SEQ ID NO: 6) (herein referred to as BCY9717);
A-(SEQ ID NO: 6)-A (herein referred to as BCY10194);
A-(SEQ ID NO: 6)-A-[K(PYA)] (herein referred to as BCY18041);
[PYA]-A-(SEQ ID NO: 6)-A-NH$_2$ (herein referred to as BCY10910); and
Ac-A-(SEQ ID NO: 6)-[K(PYA)]—NH$_2$ (herein referred to as BCY10911),
wherein PYA represents 4-pentynoic acid.

In a yet further embodiment, the peptide ligand comprises N- and/or C-terminal additions and is selected from:
A-(SEQ ID NO: 2)-A (herein referred to as BCY12027);
H$_2$N-A-(SEQ ID NO: 2)-A-[K(PYA)] (herein referred to as BCY12026);
A-(SEQ ID NO: 3)-A (herein referred to as BCY11648);
H$_2$N-A-(SEQ ID NO: 3)-A-[K(PYA)] (herein referred to as BCY12025);
Ac-A-(SEQ ID NO: 4)-A (herein referred to as BCY11279);
Ac-A-(SEQ ID NO: 5)-A (herein referred to as BCY11281);
Ac-(SEQ ID NO: 6) (herein referred to as BCY9717);
A-(SEQ ID NO: 6)-A (herein referred to as BCY10194);
[PYA]-A-(SEQ ID NO: 6)-A-NH$_2$ (herein referred to as BCY10910); and
Ac-A-(SEQ ID NO: 6)-[K(PYA)]—NH$_2$ (herein referred to as BCY10911),
wherein PYA represents 4-pentynoic acid.

The peptides of this embodiment display good binding to P-selectin (see Table 6).

In a particular embodiment, the peptide ligand is selected from: BCY11648, BCY12027, BCY12025 and BCY12026. In a further embodiment, the peptide ligand is selected from: BCY12027 and BCY12026. The peptides of these embodiments display very good binding to P-selectin, for example BCY12027 displays a high affinity for P-selectin with a K$_D$ of less than 10 nM (see Table 6).

In a further embodiment, the pharmaceutically acceptable salt is selected from the free acid or the sodium, potassium, calcium or ammonium salt.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4$^{th}$ ed., John Wiley & Sons, Inc.), which are incorporated herein by reference.

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 2)
-$C_i$-$D_1$-$A_2$-$D_3$-1Nal$_4$-$C_{ii}$-$D_5$-$V_6$-$P_7$-$S_8$-$L_9$-$P_{10}$-$C$-$_{iii}$-.

Molecular Format

N- or C-terminal extensions to the bicycle core sequence are added to the left or right side of the sequence, separated by a hyphen. For example, an N-terminal biotin-G-Sar$_5$ tail would be denoted as:

(SEQ ID NO: X)
[Biot]-G-[Sar$_5$]-A-.

For the purpose of this description, all bicyclic peptides are assumed to be cyclised with either 1,1',1"-(1,3,5-triazinane-1,3,5-triyl)triprop-2-en-1-one (TATA) or 1,1',1"-(1,4,7-triazonane-1,4,7-triyl)tris(2-chloroethan-1-one) (TCAZ) or the bromo derivative 1,1',1"-(1,4,7-triazonane-1,4,7-triyl)tris(2-bromothan-1-one) (TBAZ):

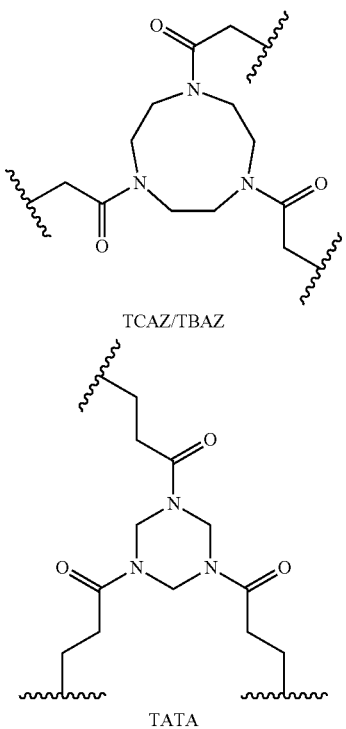

TCAZ/TBAZ

TATA and yielding a tri-substituted structure. However, as will be clear from the descriptions of the invention presented herein, cyclisation may be performed with any suitable molecular scaffold which forms covalent bonds with the reactive groups of the polypeptide such that at least two polypeptide loops are formed. Cyclisation occurs on $C_i$, $C_{ii}$, and $C_{iii}$.

In one embodiment, the molecular scaffold is TATA and the bicyclic peptide is selected from: BCY11279, BCY11281, BCY9717, BCY10194, BCY10910 and BCY10911.

In an alternative embodiment, the molecular scaffold is TCAZ and the bicyclic peptide is selected from: BCY12027, BCY11648, BCY12025 and BCY12026.

Inversed Peptide Sequences

In light of the disclosure in Nair et al. (2003) J. Immunol. 170(3), 1362-1373, it is envisaged that the peptide sequences disclosed herein would also find utility in their retro-inverso form. For example, the sequence is reversed (i.e. N-terminus become C-terminus and vice versa) and their stereochemistry is likewise also reversed (i.e. D-amino acids become L-amino acids and vice versa).

Peptide Ligand Definition

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecyl sulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g. —COOH may be —COO), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with one or more replacement amino acids, such as an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group; modification of amino acids such as cysteine, lysine, glutamate/aspartate and tyrosine with suitable amine, thiol, carboxylic acid and phenol-reactive reagents so as to functionalise said amino acids; and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal residue is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal residue is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise (3-turn conformations (Tugyi et al. (2005) PNAS, 102(2), 413-418).

In one embodiment, the modified derivative comprises removal of any amino acid residues and substitution with alanines, such as D-alanines. This embodiment provides the advantage of identifying key binding residues and removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al., *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al., Curr. Pharmaceutical Design, (2010), 16, 3185-203, and Nestor et al., Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulphur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the DLL3 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labelled reagent in place of the non-labelled reagent previously employed.

Molecular Scaffold

In one embodiment, the molecular scaffold comprises a non-aromatic molecular scaffold. References here in "non-aromatic molecular scaffold" refer to any molecular scaffold as defined herein which does not contain an aromatic (i.e. unsaturated) carbocyclic or heterocyclic ring system.

Suitable examples of non-aromatic molecular scaffolds are described in Heinis et al. (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

An example of an $\alpha\beta$ unsaturated carbonyl containing compound is 1,1',1"-(1,3,5-triazinane-1,3,5-triyl)triprop-2-en-1-one (TATA) (Angewandte Chemie, International Edition (2014), 53(6), 1602-1606).

Multimeric Binding Complexes

According to one aspect of the invention, there is provided a multimeric binding complex which comprises at least two peptide ligands, wherein at least one peptide ligand is specific for P-selectin as defined herein and said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

The present invention describes a series of multimerized bicyclic peptides with various chemical linkers and hinges of various lengths and rigidity using different sites of attachments within said bicyclic peptide which bind and activate targets (such as P-selectin) with a wide range of potency and efficacy.

It will be appreciated by the skilled person that the concept of the invention is the recognition that multiply arranged (multimeric) bicyclic peptides provide a synergistic benefit by virtue of the resultant properties of said multimeric binding complexes compared to the corresponding monomeric binding complexes which contain a single bicyclic peptide. For example, the multimeric binding complexes of the invention typically have greater levels of binding potency or functional activity (as measured herein by $EC_{50}$ values) than their monomeric counterparts. Furthermore, the multimeric binding complexes of the invention are designed to be sufficiently small enough to be cleared by the kidneys.

The complexes of the present invention find particular utility in the treatment of diseases and disorders related to cell adhesion molecules, such as those mediated by cell adhesion molecules. Such diseases and disorders include those of the blood, for example sickle cell disease or sickle cell anaemia and vaso-occlusive crisis. In one embodiment, the disease or disorder is related to sickle cell disease. In another embodiment, the disease or disorder is cancer. In a yet further embodiment, the disease or disorder is cancer metastasis. In one embodiment, the cell adhesion molecule is P-selectin. In a further embodiment, the cell adhesion molecule is E-selectin and/or L-selectin.

In a particular embodiment, at least one of said peptide ligands is specific for P-selectin and at least one of said further peptide ligands binds P-selectin. Thus, in one embodiment, at least two of said peptide ligands bind P-selectin. In a further embodiment, said two or more P-selectin molecules are present on different target cells. In an alternative embodiment, said two or more P-selectin molecules are present on the same target cell.

Thus, in certain embodiments, multimerized peptides of the invention comprise at least two peptide ligands specific for P-selectin. In a further embodiment, multimerized peptides comprise three peptide ligands specific for P-selectin. In another embodiment, the multimerized peptides comprise four peptide ligands specific for P-selectin.

In further embodiments, the cell is selected from a blood cell, such as a red blood cell. In a particular embodiment, the cell is a red blood cell affected by sickle cell disease or sickle cell anaemia. Thus, in one embodiment, the cell is a sickle red blood cell.

Without being bound by theory it is believed that multimerized peptides are able to block cell-surface molecules such as cell adhesion molecules. Thus, in one embodiment, said peptide ligands are specific for the same target. In a further embodiment, the multimeric binding complex comprises at least two identical peptide ligands. By "identical" it is meant peptides having the same amino acid sequence, most critically the same amino acid sequence refers to the binding portion of said peptide (for example, the sequence may vary in attachment position). In this embodiment, each of the peptides within the multimeric binding complex will bind exactly the same epitope upon the same target—the resultant target bound complex will therefore create a homodimer (if the multimeric complex comprises two identical peptides), homotrimer (if the multimeric complex comprises three identical peptides) or homotetramer (if the multimeric complex comprises four identical peptides), etc.

In an alternative embodiment, the multimeric binding complex comprises at least two differing peptide ligands. By "differing" it is meant peptides having a different amino acid sequence. In this embodiment, the differing peptide ligands within the multimeric binding complex will bind to different epitopes on the same target—the resultant target bound complex will therefore create a biparatopic (if the multimeric complex comprises two differing peptides), triparatopic (if the multimeric complex comprises three differing peptides) or tetraparatopic (if the multimeric complex comprises four differing peptides), etc.

It will be further appreciated that multimerized peptides will be able to block or repress cell surface molecules, such as differing cell adhesion molecules. Thus, in one embodiment, said peptide ligands are specific for different targets. It will be appreciated that in this embodiment, the multimeric binding complex comprises at least two differing peptide ligands (i.e. peptide ligands having differing amino acid sequences). In this embodiment, each of the peptides within the multimeric binding complex will bind a differing epitope upon a different target—the resultant target bound complex will therefore create a bispecific multimeric binding complex (if the multimeric complex comprises two differing peptides), trispecific multimeric binding complex (if the multimeric complex comprises three differing peptides), tetraspecific multimeric binding complex (if the multimeric complex comprises four differing peptides), etc. In a further embodiment, each of the differing epitopes and/or targets are present on the same cell.

It will be appreciated that the multimeric binding complexes of the invention may be designed to be capable of binding to a range of different targets, such as receptors. It will therefore be appreciated that for the bi-, tri- and tetra-specific multimeric binding complexes referred to hereinbefore the peptides may bind to targets on at least two differing cells (such as cells of the blood vessels, endothelial cells or other blood cells, such as other red blood cells).

The peptides within the multimeric binding complexes of the invention may be assembled via a number of differing options. For example, there may be a central hinge or branching moiety with spacer or arm elements radiating from said hinge or branch point each of which will contain a peptide. Alternatively, it could be envisaged that a circular support member may hold a number of inwardly or outwardly projecting peptides.

In one embodiment, each peptide ligand is connected to a central hinge moiety by a spacer group.

It will be appreciated that the spacer group may be linear and connect a single peptide with the central hinge moiety. Thus, in one embodiment, the multimeric binding complex comprises a compound of formula (I):

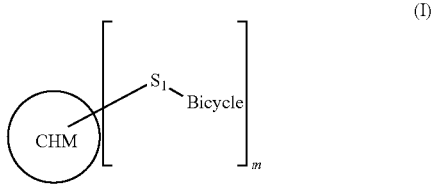

(I)

wherein CHM represents a central hinge moiety;
$S_1$ represents a spacer group;
Bicycle represents a peptide ligand as defined herein; and
m represents an integer selected from 2 to 10.

In one embodiment, m represents an integer selected from 2 to 4. In a further embodiment, m represents an integer selected from 2, 3 or 4.

When m represents 4, it will be appreciated that the central hinge moiety will require 4 points of attachment. Thus, in one embodiment, m represents 4 and CHM is a motif of formula (A):

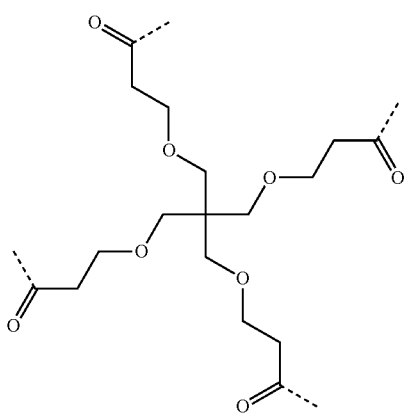

(A)

(referred to herein as Tet), wherein "-----" represents the point of attachment to each $S_1$ group.

When m represents 3, it will be appreciated that the central hinge moiety will require 3 points of attachment. Thus, in one embodiment, m represents 3 and CHM is a motif of formula (B):

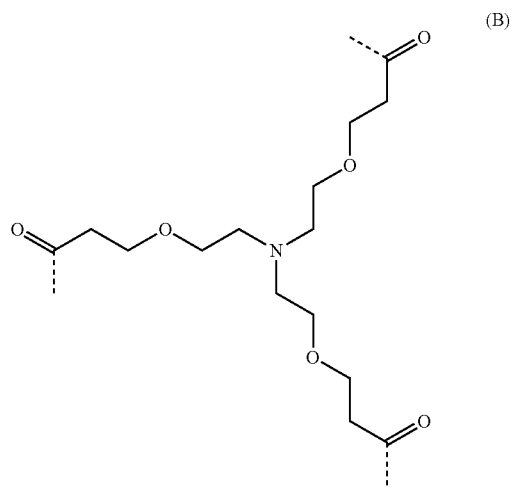

(B)

(referred to herein as TCA), wherein "-----" represents the point of attachment to each $S_1$ group.

When m represents 2, it will be appreciated that the central hinge moiety will require 2 points of attachment. Thus, in one embodiment, m represents 2 and CHM is a motif of formula (C):

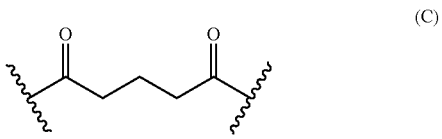 [SMILES: *C(=O)CCCC(*)=O]

(C)

(referred to herein as GTA), wherein "∼∼∼" represents the point of attachment to each $S_1$ group.

It will be readily apparent to the skilled person how alternative central hinge moieties may be constructed depending upon the value of m.

It will be appreciated that the spacer ($S_1$) may be any suitable construction to link the peptide central hinge moiety to the peptide. In one embodiment, the spacer ($S_1$) comprises a triazolyl moiety. The advantage of this embodiment is that the triazolyl moiety may be incorporated within the synthesis using commonly available "click" chemistry. Examples of suitable spacer ($S_1$) groups include one or more PEG moieties, peptide sequences, carbohydrates, lipids and the like.

In a further embodiment, the spacer ($S_1$) comprises one or more PEG moieties. References herein to "PEG" refer to a linear polymer with a regular repeat unit of the general structure: $(CH_2CH_2O)_n$— (where n represents any number, such as 1 to 30).

Thus, in a further embodiment, the spacer ($S_1$) is selected from any one of spacers $S_1A$, $S_1B$, $S_1C$, $S_1D$, $S_1E$, $S_1F$, $S_1G$ and $S_1H$:

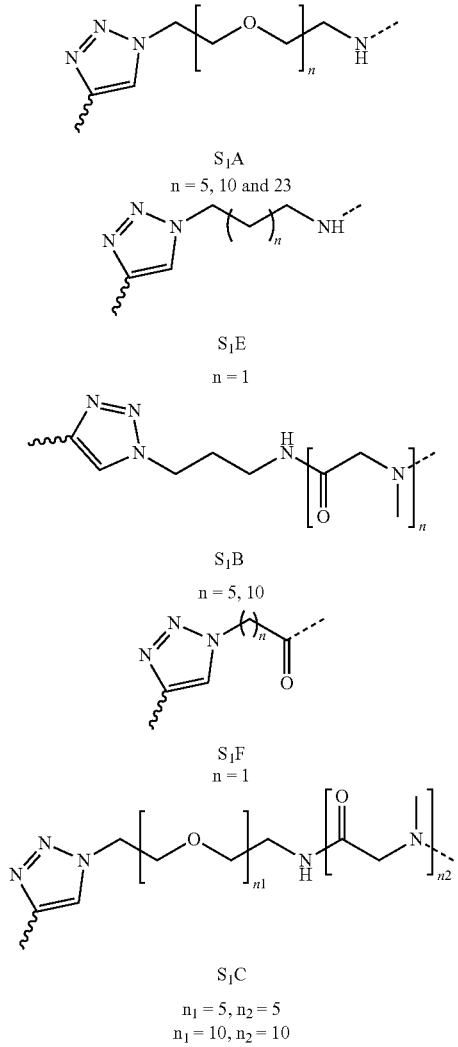

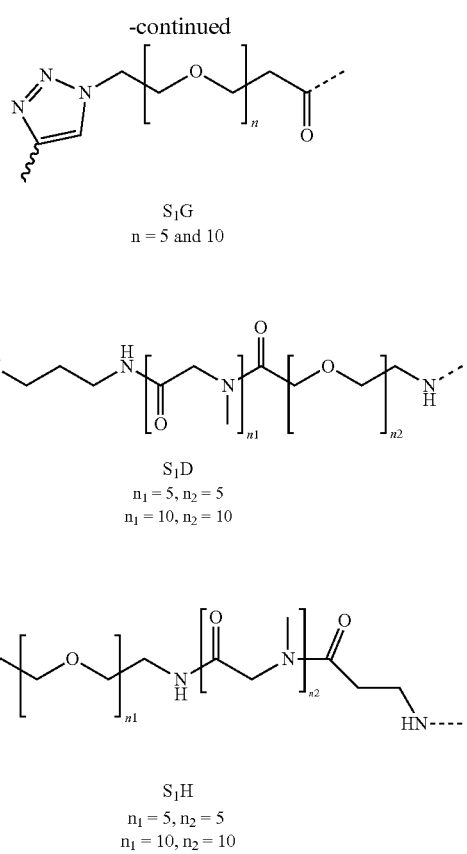

wherein " ----- " represents the point of attachment to the CHM group; and

" ~~~ " represents the point of attachment to the Bicycle group.

In a yet further embodiment, the spacer ($S_1$) is $S_1A$. In a further embodiment, n represents 5, 10 or 23.

Tetrameric Binding Complexes

In one embodiment, the multimeric binding complex comprises a tetrameric binding complex described in the following Tables 1A and 1B:

TABLE 1A

Exemplified Tetrameric Binding Complexes of the Invention

| Multimer Compound Number | Corresponding Monomer | Number of Monomers | Central Hinge Moiety | Spacer Molecule | Attachment Point |
|---|---|---|---|---|---|
| BCY5462 | BCY10910 | 4 | A (Tet) | $S_1A$: n = 10 | N-terminal Pya |
| BCY5463 | BCY10910 | 4 | A (Tet) | $S_1A$: n = 23 | N-terminal Pya |
| BCY5464 | BCY10911 | 4 | A (Tet) | $S_1A$: n = 10 | C-terminal K(Pya) |
| BCY5465 | BCY10911 | 4 | A (Tet) | $S_1A$: n = 23 | C-terminal K(Pya) |
| BCY12261 | BCY12025 | 4 | A (Tet) | $S_1A$: n = 23 | C-terminal K(Pya) |
| BCY12262 | BCY12026 | 4 | A (Tet) | $S_1A$: n = 23 | C-terminal K(Pya) |
| BCY11903 | BCY11890 | 4 | A (Tet) | $S_1A$: n = 23 | C-terminal K(Pya) |
| BCY19238 | BCY18041 | 4 | A (Tet) | $S_1A$: n = 23 | C-terminal K(Pya) |

In one embodiment, the multimeric binding complex comprises a tetrameric binding complex which is other than BCY11903 and/or BCY19238.

TABLE 1B

Preferred Exemplified Tetrameric Binding Complexes of the Invention

| Multimer Compound Number | Corresponding Monomer | Number of Monomers | Central Hinge Moiety | Spacer Molecule | Attachment Point |
|---|---|---|---|---|---|
| BCY5462 | BCY10910 | 4 | A (Tet) | $S_1A$: n = 10 | N-terminal Pya |
| BCY5463 | BCY10910 | 4 | A (Tet) | $S_1A$: n = 23 | N-terminal Pya |
| BCY5464 | BCY10911 | 4 | A (Tet) | $S_1A$: n = 10 | C-terminal K(Pya) |
| BCY5465 | BCY10911 | 4 | A (Tet) | $S_1A$: n = 23 | C-terminal K(Pya) |
| BCY12261 | BCY12025 | 4 | A (Tet) | $S_1A$: n = 23 | C-terminal K(Pya) |
| BCY12262 | BCY12026 | 4 | A (Tet) | $S_1A$: n = 23 | C-terminal K(Pya) |

Data is presented herein which demonstrates that the tetrameric binding complexes of Table 1B displayed good binding to P-selectin, with affinity $K_D$ values of less than 100 nM or less than 0.02 nM (see Table 6). In particular, data is presented herein in FIG. 2 where it can be seen that significant inhibition of white blood cell adhesion was observed for BCY12262 that compares well to the positive control antibody (crizanlizumab).

In one embodiment, the multimeric binding complex comprises a tetramer comprising four bicyclic peptides each of which are BCY10910 as defined herein, which are linked via the N-terminal Pya moiety to a spacer molecule ($S_1A$) wherein n represents 10 or 23 and wherein ($S_1A$) is linked to a central hinge moiety which is (A) as defined herein. The multimeric binding complexes according to this embodiment are referred to herein as BCY5462 and BCY5463, respectively.

In a further embodiment, the multimeric binding complex comprises a tetramer comprising four bicyclic peptides each of which are BCY10911 as defined herein, which are linked via the C-terminal Lys(Pya) moiety to a spacer molecule ($S_1A$) wherein n represents 10 or 23 and wherein ($S_1A$) is linked to a central hinge moiety which is (A) as defined herein. The multimeric binding complexes according to this embodiment are referred to herein as BCY5464 and BCY5465, respectively.

In one embodiment, the multimeric binding complex comprises a tetramer comprising four bicyclic peptides each of which are BCY12025 or BCY12026 as defined herein, which are linked via the C-terminal Lys(Pya) moiety to a spacer molecule ($S_1A$) wherein n represents 23 and wherein ($S_1A$) is linked to a central hinge moiety which is (A) as defined herein. These multimeric binding complexes are referred to herein as BCY12261 and BCY12262, respectively:

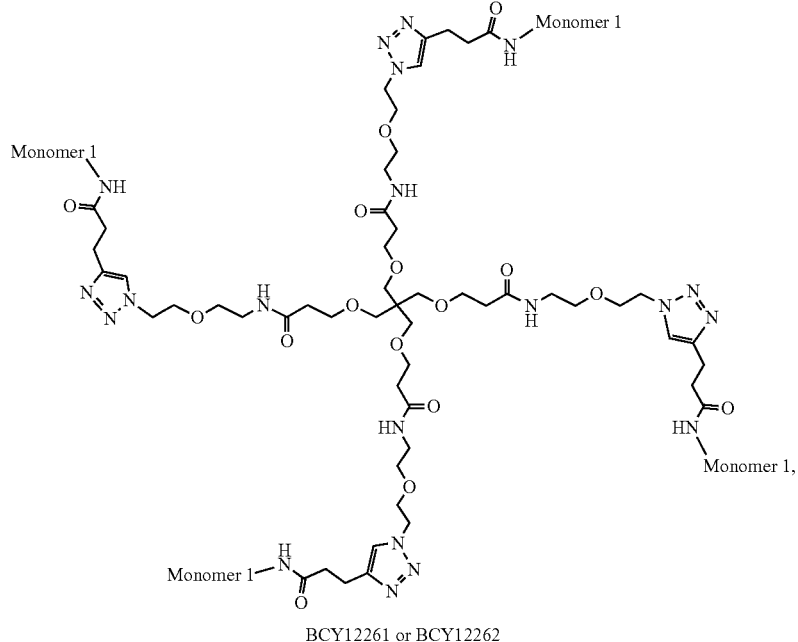

BCY12261 or BCY12262 wherein Monomer 1 represents BCY12025 or BCY12026 respectively.

Data is presented herein in Table 6 which shows that BCY12261 and BCY12262 bind P-selectin with affinity $K_D$ values of 0.019 nM and 0.017 nM respectively.

In an alternative arrangement the spacer group may be branched and thus a single spacer group may connect multiple peptides with the central hinge moiety. Thus, in an alternative embodiment, the multimeric binding complex comprises a compound of formula (II):

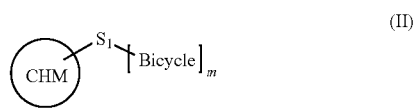

(II)

wherein CHM represents a central hinge moiety;
S₁ represents a spacer group;
Bicycle represents a peptide ligand as defined herein; and
m represents an integer selected from 2 to 10.

It will be appreciated that the peptide ligand may be attached to the spacer via a number of means. In one embodiment, the peptide ligand is conjugated to one half of a binding pair and said other half of said binding pair links each of the peptides to the spacer.

In one embodiment, said binding pair comprises biotin and streptavidin. Thus, each peptide ligand is conjugated to biotin and linked to the spacer via streptavidin.

Trimeric Binding Complexes

In one embodiment, the multimeric binding complex comprises a trimeric binding complex described in the following Tables 2A and 2B:

Data is presented herein which demonstrates that the tetrameric binding complexes of Table 2B displayed good binding to P-selectin, with affinity $K_D$ values of less than 500 nM or less than 0.5 nM (see Table 6).

In one embodiment, the multimeric binding complex comprises a trimer comprising three bicyclic peptides each of which are BCY10910 as defined herein, which are linked via the N-terminal Pya moiety to a spacer molecule (S₁A) wherein n represents 10 or 23 and wherein (S₁A) is linked to a central hinge moiety which is (B) as defined herein. The multimeric binding complexes according to this embodiment are referred to herein as BCY5458 and BCY5459, respectively.

In a further embodiment, the multimeric binding complex comprises a trimer comprising three bicyclic peptides each of which are BCY10911 as defined herein, which are linked via the C-terminal Lys(Pya) moiety to a spacer molecule (S₁A) wherein n represents 10 or 23 and wherein (S₁A) is linked to a central hinge moiety which is (B) as defined herein. The multimeric binding complexes according to this embodiment are referred to herein as BCY5460 and BCY5461, respectively.

In one embodiment, the multimeric binding complex comprises a trimer comprising three bicyclic peptides each of which are BCY12025 or BCY12026 as defined herein,

TABLE 2A

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY5458 | BCY10910 | 3 | B (TCA) | S₁A: n = 10 | N-terminal Pya |
| BCY5459 | BCY10910 | 3 | B (TCA) | S₁A: n = 23 | N-terminal Pya |
| BCY5460 | BCY10911 | 3 | B (TCA) | S₁A: n = 10 | C-terminal K(Pya) |
| BCY5461 | BCY10911 | 3 | B (TCA) | S₁A: n = 23 | C-terminal K(Pya) |
| BCY12259 | BCY12025 | 3 | B (TCA) | S₁A: n = 23 | C-terminal K(Pya) |
| BCY12260 | BCY12026 | 3 | B (TCA) | S₁A: n = 23 | C-terminal K(Pya) |
| BCY19242 | BCY11890 | 3 | B (TCA) | S₁A: n = 23 | C-terminal K(Pya) |
| BCY19239 | BCY18041 | 3 | B (TCA) | S₁A: n = 23 | C-terminal K(Pya) |

In one embodiment, the multimeric binding complex comprises a trimeric binding complex which is other than BCY19242 and/or BCY19239.

which are linked via the C-terminal Lys(Pya) moiety to a spacer molecule (S₁A) wherein n represents 23 and wherein (S₁A) is linked to a central hinge moiety which is (B) as

TABLE 2B

Preferred Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY5458 | BCY10910 | 3 | B (TCA) | S₁A: n = 10 | N-terminal Pya |
| BCY5459 | BCY10910 | 3 | B (TCA) | S₁A: n = 23 | N-terminal Pya |
| BCY5460 | BCY10911 | 3 | B (TCA) | S₁A: n = 10 | C-terminal K(Pya) |
| BCY5461 | BCY10911 | 3 | B (TCA) | S₁A: n = 23 | C-terminal K(Pya) |
| BCY12259 | BCY12025 | 3 | B (TCA) | S₁A: n = 23 | C-terminal K(Pya) |
| BCY12260 | BCY12026 | 3 | B (TCA) | S₁A: n = 23 | C-terminal K(Pya) | defined herein. These multimeric binding complexes are referred to herein as BCY12259 and BCY12260, respectively.

Data is presented herein in Table 6 which shows that BCY12259 and BCY12260 bind P-selectin with affinity $K_D$ values of 0.233 nM and 0.109 nM respectively.

Tandem Binding Complexes

In one embodiment, the multimeric binding complex comprises a tandem binding complex described in the following Tables 3A and 3B:

TABLE 3A

Exemplified Tandem Binding Complexes of the Invention

| Multimer Compound Number | Corresponding Monomer | Number of Monomers | Central Hinge Moiety | Spacer Molecule | Attachment Point |
|---|---|---|---|---|---|
| BCY5454 | BCY10910 | 2 | C (GTA) | $S_1A$: n = 10 | N-terminal Pya |
| BCY5455 | BCY10910 | 2 | C (GTA) | $S_1A$: n = 23 | N-terminal Pya |
| BCY5456 | BCY10911 | 2 | C (GTA) | $S_1A$: n = 10 | C-terminal K(Pya) |
| BCY5457 | BCY10911 | 2 | C (GTA) | $S_1A$: n = 23 | C-terminal K(Pya) |
| BCY12257 | BCY12025 | 2 | C (GTA) | $S_1A$: n = 23 | C-terminal K(Pya) |
| BCY12258 | BCY12026 | 2 | C (GTA) | $S_1A$: n = 23 | C-terminal K(Pya) |
| BCY19243 | BCY11890 | 2 | C (GTA) | $S_1A$: n = 23 | C-terminal K(Pya) |
| BCY19240 | BCY18041 | 2 | C (GTA) | $S_1A$: n = 23 | C-terminal K(Pya) |

In one embodiment, the multimeric binding complex comprises a dimeric binding complex which is other than BCY19243 and/or BCY19240.

TABLE 3B

Preferred Exemplified Tandem Binding Complexes of the Invention

| Multimer Compound Number | Corresponding Monomer | Number of Monomers | Central Hinge Moiety | Spacer Molecule | Attachment Point |
|---|---|---|---|---|---|
| BCY5454 | BCY10910 | 2 | C (GTA) | $S_1A$: n = 10 | N-terminal Pya |
| BCY5455 | BCY10910 | 2 | C (GTA) | $S_1A$: n = 23 | N-terminal Pya |
| BCY5456 | BCY10911 | 2 | C (GTA) | $S_1A$: n = 10 | C-terminal K(Pya) |
| BCY5457 | BCY10911 | 2 | C (GTA) | $S_1A$: n = 23 | C-terminal K(Pya) |
| BCY12257 | BCY12025 | 2 | C (GTA) | $S_1A$: n = 23 | C-terminal K(Pya) |
| BCY12258 | BCY12026 | 2 | C (GTA) | $S_1A$: n = 23 | C-terminal K(Pya) |

Data is presented herein which demonstrates that the dimeric binding complexes of Table 3B displayed good binding to P-selectin, with affinity $K_D$ values of about 1200 nM, less than 1000 nM, less than 500 nM or less than 0.5 nM (see Table 6).

In one embodiment, the multimeric binding complex comprises a tandem comprising two bicyclic peptides each of which are BCY10910 as defined herein, which are linked via the N-terminal PYA moiety to a spacer molecule ($S_1A$) wherein n represents 10 or 23 and wherein ($S_1A$) is linked to a central hinge moiety which is (C) as defined herein. The multimeric binding complexes according to this embodiment are referred to herein as BCY5454 and BCY5455, respectively.

In a further embodiment, the multimeric binding complex comprises a tandem comprising two bicyclic peptides each of which are BCY10911 as defined herein, which are linked via the C-terminal Lys(Pya) moiety to a spacer molecule ($S_1A$) wherein n represents 10 or 23 and wherein ($S_1A$) is linked to a central hinge moiety which is (C) as defined herein. The multimeric binding complexes according to this embodiment are referred to herein as BCY5456 and BCY5457, respectively.

In one embodiment, the multimeric binding complex comprises a tandem comprising two bicyclic peptides each of which are BCY12025 or BCY12026 as defined herein, which are linked via the C-terminal Lys(Pya) moiety to a spacer molecule ($S_1A$) wherein n represents 23 and wherein ($S_1A$) is linked to a central hinge moiety which is (C) as defined herein. These multimeric binding complexes are referred to herein as BCY12257 and BCY12258, respectively.

Data is presented herein in Table 6 which shows that BCY12257 and BCY12258 bind P-selectin with affinity $K_D$ values of 11.6 nM and 0.409 nM respectively.

Linkers

It will be appreciated that the P-selectin peptide ligand may be conjugated to the second peptide ligand via any suitable linker. Typically the design of said linker will be such that the two Bicyclic peptides are presented in such a manner that they can bind unencumbered to their respective targets either alone or while simultaneously binding to both target receptors. Additionally, the linker should permit binding to both targets simultaneously while maintaining an appropriate distance between the target cells or receptors that would lead to the desired functional outcome. The properties of the linker may be modulated to increase length, rigidity or solubility to optimise the desired functional outcome. The linker may also be designed to permit the attachment of more than one Bicycle to the same target. Increasing the valency of either binding peptide may serve to increase the affinity of the complex for the target cells or may help to block one or both of the target cell surface molecules.

In one embodiment, the linker is selected from the following sequences: —$CH_2$—, -$PEG_5$-, -$PEG_{10}$-, -$PEG_{12}$-, -$PEG_{23}$-, -$PEG_{24}$-, -$PEG_{15}$-$Sar_5$-, -$PEG_{10}$-$Sar_{10}$-, -$PEG_5$-$Sar_{15}$-, -$PEG_5$-$Sar_5$-, —B-Ala-$Sar_{20}$-, —B-Ala-$Sar_{10}$-$PEG_{10}$-, —B-Ala-$Sar_5$-$PEG_{15}$- and —B-Ala-$Sar_5$-$PEG_5$-.

Structural representations of suitable linkers are detailed below:
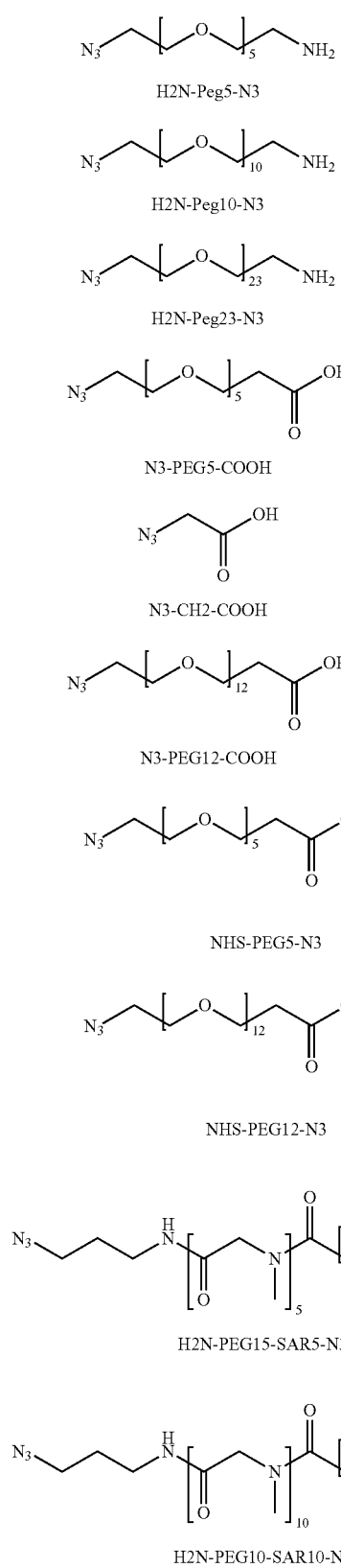
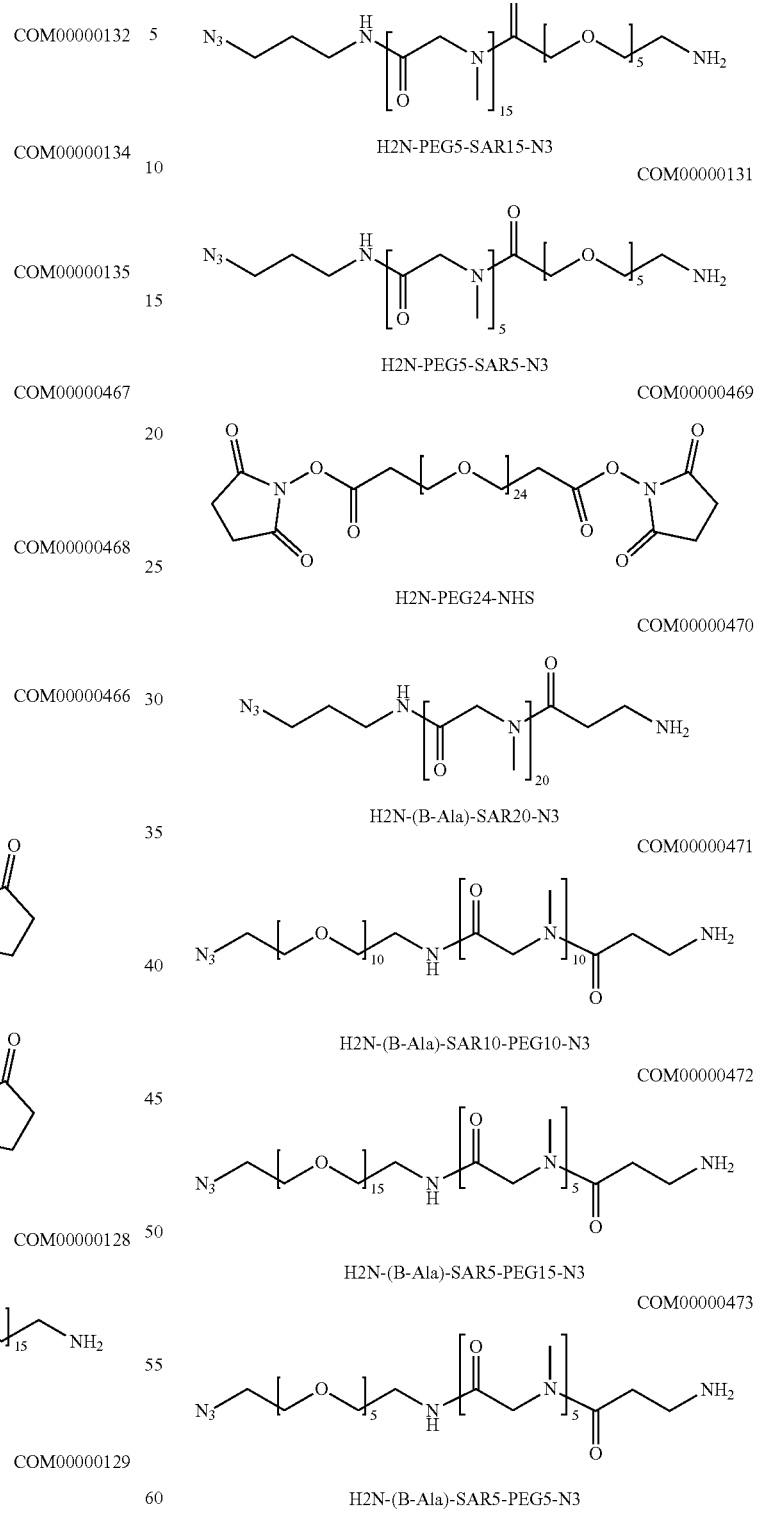
Synthesis
The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al. (supra).

Thus, the invention also relates to the manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al. Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA or TCAZ) could be added during the chemical synthesis of the first peptide so as to react with the three cysteine groups; a further cysteine or thiol could then be appended to the N- or C-terminus of the first peptide, so that this cysteine or thiol only reacted with a free cysteine or thiol of the second peptide, forming a disulphide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Drug Conjugates

According to a further aspect of the invention, there is provided a drug conjugate comprising a peptide ligand or multimeric binding complex as defined herein conjugated to one or more effector and/or functional groups.

Effector and/or functional groups can be attached, for example, to the N- and/or C-termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a t□ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al. (1994) J Biol. Chem. Volume 269 p 10444), the 18 amino acid 'model amphipathic peptide' (Oehlke et al. (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al. (2007) Nature Methods Volume 4 p 153). Other chemical strategies to add guanidinium groups to molecules also enhance cell penetration (Elson-Scwab et al. (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a t□ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a t□ half-life in the range 12 to 60 hours. In a further embodiment, it will have a t□ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one embodiment, the multimeric binding complexes of the invention contain a cleavable bond, such as a disulphide bond or a protease sensitive bond. Without being bound by theory it is believed that such a cleavable moiety deactivates the complex until it reaches the tumour microenvironment. The benefit of this embodiment provides for the complex to be reduced in size following binding to the target. In a further embodiment, the groups adjacent to the disulphide bond are modified to control the hindrance of the disulphide bond, and by this the rate of cleavage and concomitant release of the binding agent.

Published work established the potential for modifying the susceptibility of the disulphide bond to reduction by introducing steric hindrance on either side of the disulphide bond (Kellogg et al. (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on the targeting entity (here, the bicyclic peptide ligand).

Pharmaceutical Compositions

According to a further aspect of the invention, there is provided a pharmaceutical composition comprising a peptide ligand, multimeric binding complex or drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Further examples of other agents which may be administered separately or in conjunction with the peptide ligands of the invention include cytokines, lymphokines, other hematopoietic factors, thrombolytic and anti-thrombotic factors. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered intravenously. The dosage and frequency of administration will depend on the age, sex and condition of the patient, concurrent administration of other drugs, counter indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as P-selectin binding agents. According to a further aspect of the invention, there is provided a peptide ligand, multimeric binding complex, drug conjugate or pharmaceutical composition as defined herein for use in preventing, suppressing or treating a disease or disorder mediated cell adhesion molecules, such as P-selectin, E-selectin and L-selectin.

P-selectin is a cell adhesion molecule expressed on the surface of activated endothelial cells and platelets. In unactivated endothelial cells and platelets. P-selectin is stored in granules. P-selectin is involved in the recruitment of white blood cells during inflammation and the aggregation of platelets during vascular injury. Activation of platelets by thrombin results in "membrane flipping" where α-granules and dense granules are released, exposing their inner walls to the outside of the cell. Platelet aggregation is then promoted by P-selectin through platelet-fibrin and platelet-platelet binding.

P-selectin has also been shown to have a role in tumour metastasis, similar to E-selectin (Kohler et al., British Journal of Cancer 2010, 102:3). The expression of P-selectin on the surface of activated endothelial cells and platelets also aids the invasion of cancer cells into the blood stream. The formation of complexes of activated platelets with tumour cells in the vasculature prevents the recognition of tumour cells by macrophages, shielding them from recognition by the immune system. It has been shown that a reduction in circulating platelets could reduce cancer metastasis (Gasic G L, Cancer Metastasis Reviews 1984, 3:2). Furthermore, the related cell adhesion molecule, E-selectin, has been shown to be constitutively expressed on the surface of bone marrow endothelium, indicating a route by which tumour cells may metastasise preferentially to the bone.

The role of P-selectin in cardiovascular conditions such as cardiac inflammation and fibrosis, coronary heart disease, hypertension and atrial fibrillation has also been reported (Liu el al., Molecular Medicine Reports 2016, 13(6) and Blann et at, European Heart Journal 2003, 24(24)), For example, increased P-selectin expression has been demonstrated on active atherosclerotic plaques and animals lacking P-selectin have been seen to have decreased tendency to form atherosclerotic plaques. Furthermore, the P-selectin antagonist, inclacumab reduces myocardial damage after percutaneous coronary intervention in non-ST-segment elevation myocardial infarction patients and platelet-leukocyte aggregates were inhibited (Stahli et al., Journal of the American Heart Association 2016, 16:5(11) and Schmitt et al., Jornal of Cardiovascular Pharmacology 2015, 65(6)). Therefore, the antagonism or blocking of P-selectin will likely find therapeutic benefit.

In one embodiment, the P-selectin is mammalian P-selectin. In a further embodiment, the mammalian P-selectin is human P-selectin.

P-selectin peptides will be primarily (but not exclusively) used to antagonistically block P-selectin or a related cell adhesion molecule (e.g. E-selectin and/or L-selectin), and consequently activated endothelial cells and platelets. It will be appreciated that such antagonism will find particular utility in the prevention, suppression and/or treatment of vaso-occlusive crisis or other disease/disorder related to sickle cell disease or sickle cell anaemia.

P-selectin peptides may also be used to antagonistically block P-selectin or a related cell adhesion molecule (e.g. E-selectin and/or L-selectin) binding to glycoproteins or glycolipid ligands expressed on a cancer cell or cancer, and consequently the metastasis or tumour invasion of said cancer cell or cancer. Such cancers include, but are not limited to early or late stage human malignancies, which include solid tumours such as Non-Small Cell Lung Carcinomas (NSCLC), breast cancers, including triple negative breast cancers (TNBC), ovarian cancers, prostate cancers, bladder cancers, urothelial carcinomas, colorectal cancers, head and neck cancer, Squamous Cell Carcinoma of the Head and Neck (SCCHN), melanomas, pancreatic cancers, and other advanced solid tumours. The cancer may also be selected from a blood cancer.

The term "solid tumour" as used herein is defined as an abnormal growth of tissues without much liquid mass in it, while non-solid tumours are generally dispersed cancers without any or significant solid masses. Examples of solid tumours are carcinomas, sarcomas and lymphomas. Blood cancers (leukaemias) such as acute myeloid leukaemia (AML), Acute lymphocytic (or lymphoblastic) leukaemia (ALL) are non-solid tumours. P-selectin peptides or the complexes defined herein may be used as a monotherapy agent in the aforementioned cancer indications to block, prevent or reduce tumour cell metastasis. In addition to use as a monotherapy agent in cancer, P-selectin peptides, as well as complexes and conjugates thereof as defined herein, may be used in combination with immunotherapy agents, such as anti-PD-1 and anti-CTLA4 agents. Additional therapeutic applications of P-selectin peptides, complexes and conjugates thereof include, but are not restricted to, mono or combination therapies with radiation cancer treatments, and cancer vaccines. Non-cancerous therapeutic applications of P-selectin peptides either as monotherapy or in combination therapy, include but are not limited to, diseases and disorders related to sickle cell disease/anaemia, such as vaso-occlusive crisis.

It will be appreciated that P-selectin peptides may be useful in the treatment of conditions characterised by intercellular adhesion mediated by P-selectin or a related cell adhesion molecule (e.g. E-selectin and/or L-selectin). Such conditions include, without limitation: post-ischemic leukocyte-mediated tissue damage (reperfusion injury), such as that related to myocardial infarction or transplant; myocardial infarction; bacterial or viral infection; metastatic conditions; inflammatory disorders, such as arthritis; acute respiratory distress syndrome (ARDS); asthma; emphysema; delayed type hypersensitivity reaction; systemic lupus erythematosus (SLE); thermal injury; autoimmune thyroiditis; experimental allergic encephalomyelitis (EAE); multiple sclerosis (MS); multiple organ injury syndrome secondary to trauma; diabetes; Reynaud's syndrome; neutrophilic dermatosis (Sweet's syndrome); inflammatory bowel disease (MD); Grave's disease; glomerulonephritis; gingivitis; periodontitis; haemolytic uremic syndrome; ulcerative colitis; Crohn's disease; neurotizing enterocolitis; granulocyte transfusion associated syndrome; and cytokine-induced toxicity. Further examples of conditions or treatments in which P-selectin peptides may find utility include: organ transplantation, including to prepare organs prior to transplantation and to reduce transplant rejection; haemodialysis; and leukapheresis.

Thus, in one embodiment, the bicyclic peptides of the invention find utility in and may be used for the treatment of vaso-occlusive crisis. In a further embodiment, the bicyclic peptides may be used in the treatment or prevention of metastasis. In a yet further embodiment, the bicyclic peptides may be used in the treatment or prevention of cardiac inflammation, fibrosis and atherosclerotic plaques.

It will be appreciated that multimeric binding complexes as defined herein which comprise at least one peptide ligand which binds to a cell adhesion molecule, such as P-selectin, on endothelial cells will also be useful in the treatment of cancer and non-cancer diseases and disorders, such as vaso-occlusive crisis, cardiac inflammation, fibrosis and atherosclerotic plagues.

It will also be appreciated that multimeric binding complexes as defined herein which comprise at least one peptide ligand which binds to a cell adhesion molecule, such as P-selectin, on endothelial cells will also be useful in the treatment of COVID-19.

COVID-19 is primarily a respiratory condition, it has also been viewed as a multi-system disease. Abundant evidence reveals that the SARS-CoV-2 virus can attack organs and tissues that express angiotensin-converting enzyme 2 (ACE2) receptor, which include heart, renal, liver, pancreas, gastrointestinal tract, brain, and endothelial cells, subsequently trigger inflammatory cascades and blood clotting. COVID-19 may cause severe vascular complications, which consequently lead to endothelial dysfunction, overproduction cytokines, and pathological cellular interactions. Red blood cells (RBCs) are the most abundant cellular components of blood and responsible for the transportation of oxygen, removal of waste, and delivery of nutrients throughout the human body. Prior studies suggested that SARS-CoV-2 infection can also damage RBC membrane, decrease hemoglobin (Hb) concentration, and prevent red blood cell (RBC) formation, resulting in serious anemia and irreversible organ damage. Thus, one plausible pathogenic mechanism of the "post-COVID syndrome" is the combination of red blood cell abnormality and build-up of inflammatory factors, which in turn cause inadequate oxygen delivery, hypercoagulation, and vascular complications, and contribute, at least in part, to the prolonged symptoms observed in a significant portion of COVID patients, including chronic fatigue, excise intolerance, joint and chest pain, and brain fog. Since dysregulation of P-selectin is a key factor of COVID-19 pathology, inhibition of inflammation-driven, P-selectin mediated blood cell adhesion to endothelium could be a promising therapeutic strategy to mitigate adverse symptoms, facilitate function recovery, and improve long-term health of millions of individuals affected by this disease.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods

Preparation of Monomeric Bicyclic Peptide Ligands (General Method)

Bicycle peptides were synthesized on Rink amide resin using standard Fmoc (9-fluorenylmethyloxycarbonyl) solid-phase peptide synthesis, either by manual coupling (for large scale) or using a Biotage SyroII automated peptide synthesizer (for small scale). Following TFA-based cleavage from the resin, peptides were precipitated with diethyl ether and dissolved in 50:50 acetonitrile/water. The crude peptides (at ~1 mM concentration) were then cyclized with 1.3 equiv. of the scaffold, using ammonium bicarbonate (100 mM) as a base. Completion of cyclization was determined by matrix-assisted laser desorption ionization time-of-flight (MALDI-TOF) or LC-MS. Once complete, the cyclization reaction was quenched using N-acetyl cysteine (10 equiv. with respect to the peptide), and the solutions were lyophilized. The residue was dissolved in an appropriate solvent and purified by RP-HPLC. Peptide fractions of sufficient purity and the correct molecular weight (verified by either MALDI-TOF and HPLC or LC-MS) were pooled and lyophilized. Concentrations were determined by UV absorption using the extinction coefficient at 280 nm, which was based on Trp/Tyr content.

All amino acids, unless noted otherwise, were used in the L-configurations.

Preparation of Dimeric/Tandem Binding Complexes (Exemplified with BCY5455)

Synthesis of Hinge GTA(PEG23-N3):

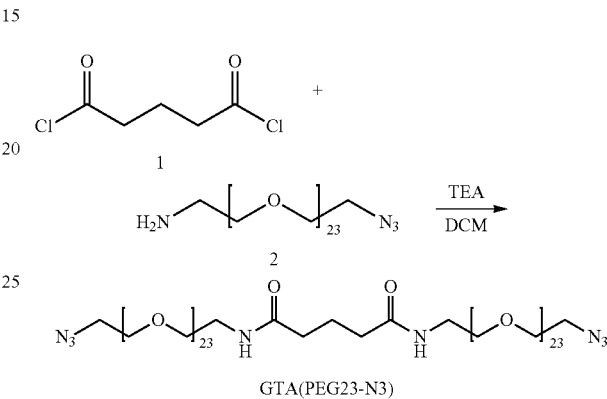

To a solution of compound 1 (10 mg, 59.17 μmol, 7.58 μL, 1 eq.) in DCM (2 mL) was added Triethylamine (17.96 mg, 177.51 μmol, 24.71 μL, 3 eq.). Compound 2 (132.0 mg, 120.08 μmol, 2.03 eq.) was then added. The mixture was stirred at 30° C. for 2 hr. LC-MS showed compound 1 was consumed completely and one main peak with desired m/z was detected. The reaction mixture was concentrated under reduced pressure to remove solvent to give a residue. The residue was purified by preparative HPLC. GTA(PEG23-N3) (82 mg, 35.02 μmol, 59.19% yield, 98% purity) was obtained as a white solid. (MW: 2294.69. Observed m/z: 1156.31 [M+H$_3$O+H]$^{2+}$).

Preparation of BCY5455:

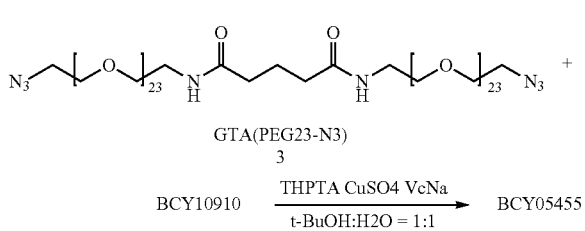

To a solution of GTA(PEG23-N3) (10 mg, 4.36 μmol, 1 eq.), BCY10910 (20.00 mg, 9.72 μmol, 2.23 eq.) and THPTA (0.4 M, 10.89 μL, 1 eq.) was dissolved in t-BuOH/H$_2$O (1:1, 2 mL, pre-degassed and purged with N$_2$ 3 times), and then CuSO4 (0.4 M, 10.89 μL, 1 eq.) and VcNa (0.4 M, 21.79 μL, 2 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 12 hr under N$_2$ atmosphere. LC-MS showed compound 3 was consumed completely and one main peak with desired m/z was detected. The residue was purified by preparative HPLC. BCY5455 (13.6 mg, 2.07 μmol, 47.56% yield, 97.70% purity) was obtained as a white solid. (MW: 6411.26 observed m/z: 1603.1 [M+4H]$^{4+}$, 1282.4 [M+5H]$^{5+}$, 1068.95 [M+6H]$^{6+}$).

Preparation of Trimeric Binding Complexes (Exemplified with BCY12259)

Synthesis of Hinge TCA(PEG23-N3):

To a solution of compound 1 (32 mg, 79.63 μmol, 1.0 eq., HCl) and compound 2 (264.00 mg, 240.15 μmol, 3.02 eq.) in DMF (2 mL) was added HOBt (35.84 mg, 265.24 μmol, 3.33 eq.), EDCI (51.20 mg, 267.08 μmol, 3.35 eq.), DMAP (29.19 mg, 238.90 μmol, 3.0 eq.) and DIPEA (61.75 mg, 477.81 μmol, 83.23 μL, 6.0 eq.). The mixture was stirred at 25-30° C. for 12 hr. LC-MS showed compound 1 was consumed completely and one main peak with desired m/z was detected. The reaction mixture was concentrated under reduced pressure to remove solvent to give a residue. The residue was purified by preparative HPLC. TCA(PEG23-N3) (214 mg, 53.36 μmol, 67.01% yield, 90% purity) was obtained as a light yellow oil. (MW: 3609.23 observed m/z: 1214 [M+2H$_3$O+H]$^{3+}$).

Preparation of BCY12259:

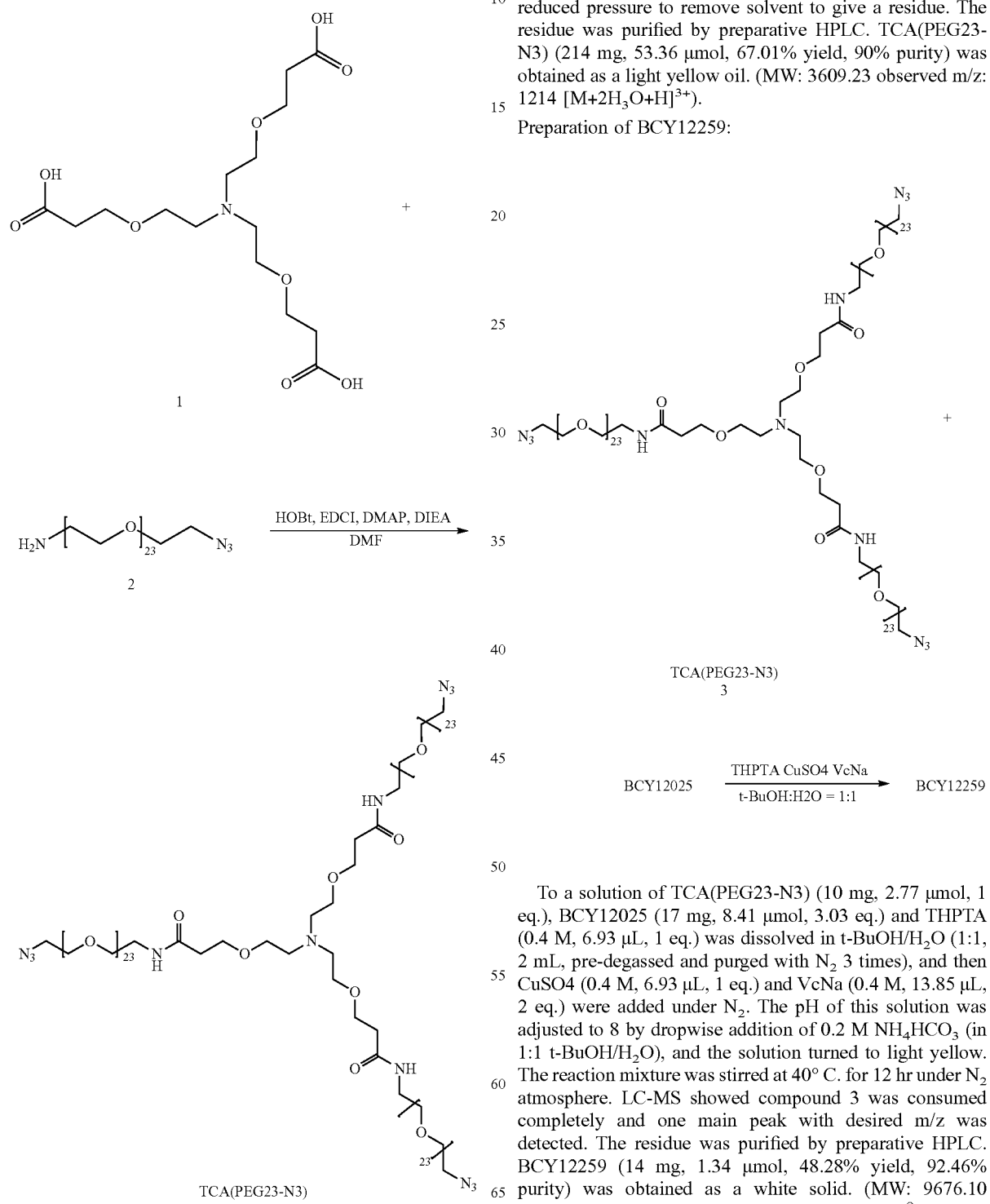

To a solution of TCA(PEG23-N3) (10 mg, 2.77 μmol, 1 eq.), BCY12025 (17 mg, 8.41 μmol, 3.03 eq.) and THPTA (0.4 M, 6.93 μL, 1 eq.) was dissolved in t-BuOH/H$_2$O (1:1, 2 mL, pre-degassed and purged with N$_2$ 3 times), and then CuSO4 (0.4 M, 6.93 μL, 1 eq.) and VcNa (0.4 M, 13.85 μL, 2 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 12 hr under N$_2$ atmosphere. LC-MS showed compound 3 was consumed completely and one main peak with desired m/z was detected. The residue was purified by preparative HPLC. BCY12259 (14 mg, 1.34 μmol, 48.28% yield, 92.46% purity) was obtained as a white solid. (MW: 9676.10 observed m/z: 1382.2 [M+7H]$^{7+}$, 1209.3 [M+8H]$^{9+}$, 1075.1 [M+9H]$^{9+}$, 967.3 [M+10H]$^{10+}$).

Preparation of Tetrameric Binding Complexes (Exemplified with BCY5464)

Synthesis of Hinge TET(PEG10-N3):

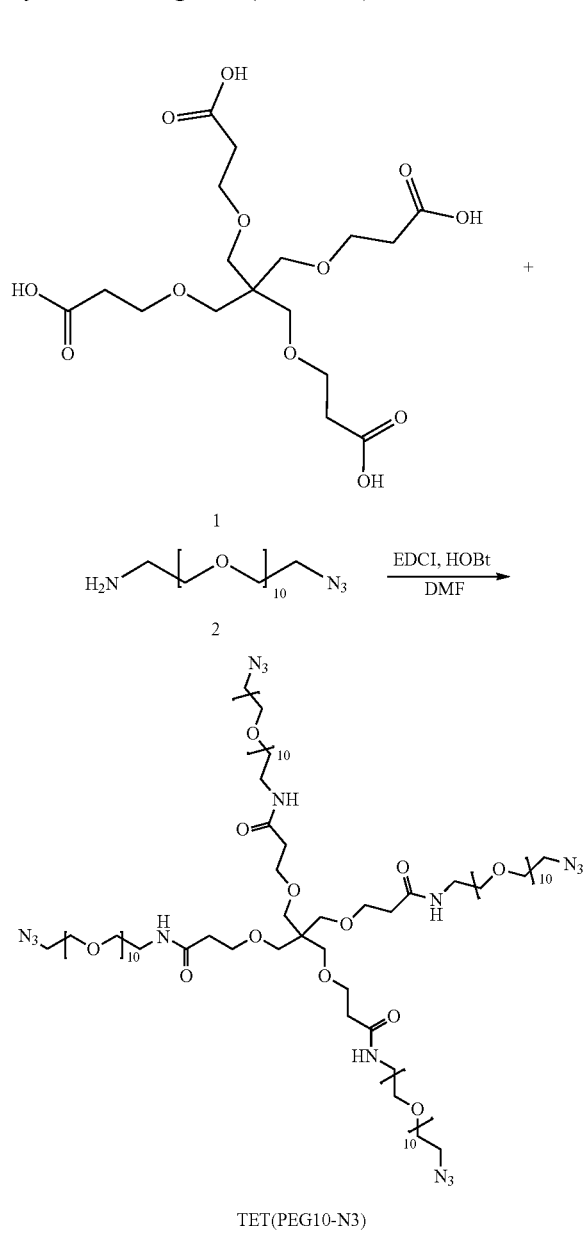

TET(PEG10-N3)

A mixture of compound 1 (52.0 mg, 122.53 μmol, 1 eq.), compound 2 (273.0 mg, 518.40 μmol, 4.23 eq.), EDCI (117.5 mg, 612.64 μmol, 5.0 eq.), and HOBT (72.8 mg, 539.12 μmol, 4.08 eq.) was dissolved in DMF (2 mL), and then DIPEA (126.7 mg, 980.22 μmol, 170.74 μL, 8.0 eq.) was added and the solution mixed well. The mixture was stirred at 25° C. for 12 hr. LC-MS showed one main peak with desired m/z. The reaction mixture was concentrated under reduced pressure to remove solvent to give a residue. The residue was purified by preparative HPLC. TET(PEG10-N3) (147.8 mg, 55.79 μmol, 45.53% yield, 92.81% purity) was obtained as a white solid. (MW: 2458.81. observed m/z: 810.7 $[M-28+3H]^{3+}$).

Preparation of BCY5464:

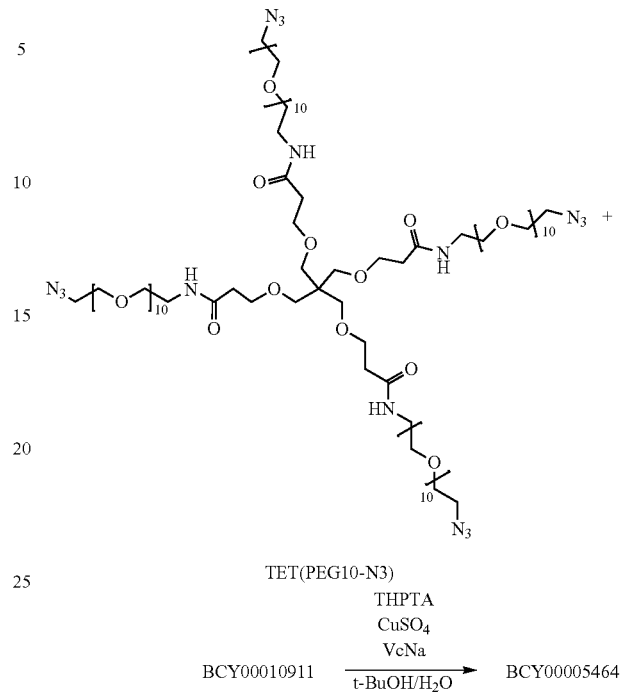

A solution of TET(PEG10-N3) (5 mg, 2.03 μmol, 1 eq.), BCY10911 (19 mg, 8.81 μmol, 4.33 eq.) and THPTA (0.4 M, 5.0 μL, 1 eq.) in t-BuOH/$H_2O$ (1:1, 2 mL, pre-degassed and purged with $N_2$) was prepared. CuSO4 (0.4 M, 5.0 μL, 1 eq.) and VcNa (0.4 M, 10.0 μL, 2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 16 hr under $N_2$ atmosphere. LC-MS showed compound 3 was consumed completely and one main peak with desired m/z was detected. The crude reaction was combined and purified by preparative HPLC. BCY5464 (12.6 mg, 92.6% purity) was obtained as a white solid. (MW: 11088.49 observed m/z: 1233.6 $[M+9H]^{9+}$, 1387.2 $[M+8H]^{8+}$).

It will be appreciated that, in general, all multimeric binding complexes of the invention may be prepared in accordance with these methods using the appropriate bicyclic peptide ligand(s).

Analytical Data

The following multimeric binding complexes of the invention were analysed using mass spectrometry and HPLC and the data are shown in Tables 4 and 5 below.

HPLC setup was as follows:

Methods A, B, and E:
Mobile Phase: A: 0.1% TFA in $H_2O$ B: 0.1% TFA in ACN
Flow: 1.0 ml/min
Column: Gemini-NX C18 5 μm 110 A 150*4.6 mm
Instrument: Agilent 1200 HPLC-BE(1-614)
Gradients:

| Method | Gradient Description |
|--------|----------------------|
| A | 25-55% B over 20 minutes |
| B | 20-50% B over 20 minutes |
| E | 30-60% B over 20 minutes |

Method C:
  Mobile Phase: A: 0.1% TFA in H$_2$O B: 0.1% TFA in ACN
  Flow: 0.4 ml/min
  Column: Kintex 1.7 μm C18 100 A 2.1 mm*150 mm
  Instrument: Agilent UPLC 1290
  Column temperature: 30° C.
  Gradient:

| Time (min) | % A | % B |
| --- | --- | --- |
| 0 | 75 | 25 |
| 10 | 45 | 55 |
| 10.01 | 10 | 90 |
| 12 | 10 | 90 |

Method D:
  Mobile phase: 0.1% TFA AcN/Water
  Flow: 1.00 ml/min
  Column: KINETEXPSC18
  Instrument: Aglient LC2
  Gradient: 5-95% B in 15.5 minutes

TABLE 4

HPLC and Mass Spectrometry Data for Monomeric Bicycle Peptide Ligands of the Invention

| Monomer ID | Molecular Weight | Mass Spectrometry - Observed m/z | HPLC Retention Time (min) | Method |
| --- | --- | --- | --- | --- |
| BCY12027 | 1825.05 | 912.6 [M + 2H]$^{2+}$ | 9.82 | B |
| BCY11648 | 1814.03 | 907.58 [M + 2H]$^{2+}$ | 8.42 | B |
| BCY11279 | 2031.25 | 1016.64 [M + 2H]$^{2+}$ | 6.30 | D |
| BCY11281 | 2034.26 | 1018.03 [M + 2H]$^{2+}$ | 6.20 | D |
| BCY09717 | 1878.08 | 939.75 [M + 2H]$^{2+}$ | 5.95 | D |
| BCY10194 | 1978.21 | 989.4 [M + 2H]$^{2+}$ | 10.08 | B |
| BCY10910 | 2058.29 | 1029.14 [M + 2H]$^{2+}$ | 14.03 | B |
| BCY10911 | 2157.42 | 1079.65 [M + 2H]$^{2+}$ | 10.31 | A |
| BCY12025 | 2022.28 | 1011.16 [M + 2H]$^{2+}$ | 9.58 | B |
| BCY12026 | 2033.31 | 1016.64 [M + 2H]$^{2+}$ | 10.91 | B |
| BCY11890 | 2197.5 | 732.9 [M + 3H]$^{3+}$, 1099.4 [M + 2H]$^{2+}$ | 9.47 | A |
| BCY18041 | 2186.5 | 729.5 [M + 3H]$^{3+}$, 1093.9 [M + 2H]$^{2+}$ | 11.10 | B |

TABLE 5

HPLC and Mass Spectrometry Data for Multimeric Binding Complexes of the Invention

| Complex ID | Molecular Weight | Mass Spectrometry - Observed m/z | HPLC Retention Time (min) | Method |
| --- | --- | --- | --- | --- |
| BCY5454 | 5265.91 | 1754.7 [M + 3H]$^{3+}$, 1316.4 [M + 4H]$^{4+}$, 1053.6 [M + 5H]$^{5+}$ | 12.32 | A |
| BCY5455 | 6411.28 | 1603.1 [M + 4H]$^{4+}$, 1282.4 [M + 5H]$^{5+}$, 1068.95 [M + 6H]$^{6+}$ | 13.06 | A |
| BCY5456 | 5464.18 | 1822.4 [M + 3H]$^{3+}$, 1367.2 [M + 4H]$^{4+}$, 1093.5 [M + 5H]$^{5+}$ | 5.89 | C |
| BCY5457 | 6609.54 | 1322.3 [M + 5H]$^{5+}$, 1101.9 [M + 6H]$^{6+}$, 944.65 [M + 7H]$^{7+}$ | 12.78 | A |
| BCY12257 | 6339.26 | 1584.6 [M + 4H]$^{4+}$, 1267.7 [M + 5H]$^{5+}$, 1056.5 [M + 6H]$^{6+}$, 905.6 [M + 7H]$^{7+}$ | 9.04 | A |
| BCY12258 | 6361.31 | 1273.1 [M + 5H]$^{5+}$, 1063.7 [M + 6H]$^{6+}$, 909.5 [M + 7H]$^{7+}$ | 13.43 | B |
| BCY5458 | 8066.07 | 1345.0 [M + 6H]$^{6+}$, 1153.14 [M + 7H]$^{7+}$ | 12.63 | A |
| BCY5459 | 9784.12 | 1223.3 [M + 8H]$^{8+}$, 1087.6 [M + 9H]$^{9+}$ | 13.32 | A |
| BCY5460 | 8363.47 | 1674.2 [M + 5H]$^{5+}$, 1394.4 [M + 6H]$^{6+}$ | 12.73 | A |
| BCY5461 | 10081.52 | 1262.83 [M + 8H]$^{8+}$, 1124.36 [M + 9H]$^{9+}$ | 13.25 | A |
| BCY12259 | 9676.1 | 1382.2 [M + 7H]$^{7+}$, 1209.3 [M + 8H]$^{8+}$, 1075.1 [M + 9H]$^{9+}$, 967.3 [M + 10H]$^{10+}$ | 9.03 | A |
| BCY12260 | 9709.16 | 1386.5 [M + 7H]$^{7+}$, 1213.3 [M + 8H]$^{8+}$, 1078.4 [M + 9H]$^{9+}$, 970.9 [M + 10H]$^{10+}$ | 10.03 | A |
| BCY5462 | 10691.99 | 1188.41 [M + 9H]$^{9+}$ | 14.14 | A |
| BCY5463 | 12996.75 | 1855.2 [M + 7H]$^{7+}$, 1299.4 [M + 10H]$^{10+}$ | 14.76 | A |
| BCY5464 | 11088.51 | 1585.6 [M + 7H]$^{7+}$ | 14.32 | A |
| BCY5465 | 13379.35 | 1673.4 [M + 8H]$^{8+}$ | 14.56 | A |
| BCY12261 | 12838.69 | 1427.4 [M + 9H]$^{9+}$, 1286.6 [M + 10H]$^{10+}$, 1169.6 [M + 11H]$^{11+}$ | 9.91 | A |
| BCY12262 | 12882.78 | 1611.3 [M + 8H]$^{8+}$, 1432.3 [M + 9H]$^{9+}$, 1290.6 [M + 10H]$^{10+}$, 1173.5 [M + 11H]$^{11+}$ | 10.95 | A |
| BCY11903 | 13539 | 13557 (TOF deconvoluted mass) | 12.58 | A |
| BCY19238 | 13495 | 13495 (TOF deconvoluted mass) | 11.14 | A |
| BCY19242 | 10202 | 10202 (TOF deconvoluted mass) | 8.78 | E |
| BCY19239 | 10169 | 10169 (TOF deconvoluted mass) | 13.73 | B |
| BCY19243 | 6689.7 | 6689 (TOF deconvoluted mass) | 11.44 | A |
| BCY19240 | 6667.6 | 6668 (TOF deconvoluted mass) | 13.63 | B |

Biological Data
1. SPR Binding Assay

Biacore experiments were performed to determine ka (M−1s−1), kd (s−1), KD (nM) values of monomeric peptides binding to human Selectin proteins. Recombinant biotinylated human P-Selectin protein was used. For analysis of binding, either a Biacore 3000 or 5200 instrument was used with a CMS sensor chip (GE Healthcare). For sensor chip surface preparation, streptavidin was immobilized on the chip using standard amine-coupling chemistry at 25° C. with HBS-N (10 mM HEPES, 0.15 M NaCl, pH 7.4) as the running buffer. The carboxymethyl dextran surface was activated with a 12 min injection of a 1:1 ratio of 0.4 M 1-ethyl-3-(3-dim ethyl aminopropyl) carbodiimide hydrochloride (EDC)/0.1 M N-hydroxy succinimide (NHS) at a flow rate of 10 μl/min. For capture of streptavidin, protein was diluted to 0.2 mg/ml in 10 mM sodium acetate (pH 4.5) and captured by injecting 70 μl onto the activated chip surface. Residual activated groups were blocked with a 7 min injection of 1 M ethanolamine (pH 8.5). Biotinylated protein stock was diluted 1:100 in HBS-N and captured on one flow cell at 5 μl/min to a level of 1000-1500 RU. Buffer was changed to PBS/0.05% Tween 20 and a dilution series of the peptides was prepared in this buffer with a final DMSO concentration of 0.5%. The top concentration of the analyte varied from 200 nM to 50 μM; depending on predicted affinity of the interaction. In all cases a titration was performed with either seven 2-fold dilutions or five 3-fold dilutions. The SPR analysis was run at 25° C. with a flow rate of 50-80 μl/min with 60 seconds association and a suitable disassociation period (100-900 seconds). Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using mass transport model allowing for mass transport effects where appropriate.

TABLE 6

Affinity $K_D$ Values Determined by SPR

| Peptide Number | $K_D$ (nM) |
|---|---|
| BCY12027 | 5.36 |
| BCY11648 | 128 |
| BCY11279 | 690 |
| BCY11281 | 2020 |
| BCY9717 | 7600 |
| BCY10194 | 9500 |
| BCY5454 | 400 |
| BCY5455 | 1250 |
| BCY5456 | 500 |
| BCY5457 | 969 |
| BCY5458 | 400 |
| BCY5459 | 169 |
| BCY5460 | 239 |
| BCY5461 | 230 |
| BCY5462 | 88.0 |
| BCY5463 | 53.0 |
| BCY5464 | 37.3 |
| BCY5465 | 140 |
| BCY12257 | 11.6 |
| BCY12258 | 0.409 |
| BCY12259 | 0.233 |
| BCY12260 | 0.109 |
| BCY12261 | 0.019 |
| BCY12262 | 0.017 |

2. Receptor Ligand Inhibition Assay

Bicycle test samples, SelG1 (Crizanlizumab) were serially diluted maintaining 0.5% DMSO in assay buffer (25 mM HEPES, 121 mM NaCl, 5.4 mM KCl, 0.8 mM $MgCl_2$, 1.8 mM $CaCl_2$), 6 mM $NaHCO_2$, 5.5 mM glucose, 1% BSA, pH7.4) and transferred to 384 well clear bottom plates (Corning, 3712) with a final volume of 6 μL. 64, of P-Selectin in imaging buffer (25 mM HEPES, 121 mM NaCl, 5.4 mM KCl, 0.8 mM $MgCl_2$, 1.8 mM $CaCl_2$), 6 mM $NaHCO_2$, 5.5 mM glucose, pH7.4) was added to give a 5 nM final concentration and incubated at room temperature for 15 minutes. HL-60 cells (ATCC, CCL-240) mixed with 1 μg/mL far red labelled wheat germ agglutinin (WGA, ThermoFisher W21404) and 1 μg/mL AlexaFluor 488-streptavidin (Invitrogen S11223) were added to the plate and incubated for 2 hours at room temperature in the absence of light. Staining and antibody binding were quantified by simultaneously scanning the microplates with 488 nm and 640 nm lasers on a mirrorball microplate cytometer, AF488 on FL2 triggering on AF647-WGA on FL4. Data was analysed in Dotmatics, using a four parameter logistic fit to generate IC50 values and % response. Percent inhibition was calculated using 100–% response at top concentration. Selected peptides were tested in this assay and the results ($IC_{50}$ and % inhibition data) are shown in Table 7 where data displayed is the geomean of n=3.

TABLE 7

Effect of P-Selectin binding Bicycles on the P-Selectin:PSGL1 interaction

| BCY number | $IC_{50}$ (nM) | Inhibition at top concentration (%) |
|---|---|---|
| SelG1 | 4.75 | 96 |
| BCY9717 | >10875 | 20 |
| BCY11279 | >3539 | 24 |
| BCY11648 | >117 | 37 |
| BCY12027 | >36.8 | 36 |
| BCY12257 | >78.4 | 54 |
| BCY12258 | >97.7 | 57 |
| BCY12259 | 14.4 | 61 |
| BCY12260 | 9.62 | 64 |
| BCY12261 | 10.4 | 68 |
| BCY12262 | 3.29 | 68 |

3. Cell Adhesion Bioassay Characterization of BCY12262

Background

In flow adhesion assays (FIG. 1) microfluidic channels are coated with proteins that mimic the endothelium, including specific binding receptors of interest (such as P-Selectin). Then a sample of cells and test articles is flown at physiologically relevant flow conditions through the channel and the number of cells that adhere to the channel surface is quantified. P-selectin is a cell adhesion molecule on the surfaces of activated endothelial cells. White Blood Cells (WBC) materially contribute to adhesion on P-selectin in Whole Blood. White Blood Cells are isolated from the blood sample and the concentration normalized to 5 million/mL.

Methodology

A commercial well plate microfluidic flow adhesion system, BioFlux 10002 (Fluxion Bio, San Francisco, CA, USA) was utilized. Isolated. WBC suspension from a single convalescent COVID-19 patient (at 5 million cells/ml in Hank's Balanced Salt Solution buffer) was perfused through P-selectin (5 μg/ml)-coated microfluidic channels (350 μm wide×70 μm tall) using pulsatile (1·67 Hz) shear stress (1 dyne/$cm^2$) and washed with the buffer at the same flow rate to eliminate non-adhering cells. Images were acquired with a high-resolution CCD camera and analyzed with Montage imaging software (Molecular Devices, Downingtown, PA, USA). An adhesion index (AI) was established for each sample by quantifying adherent cells within a standard viewing area (cells/$mm^2$).

Results

Figure 2:
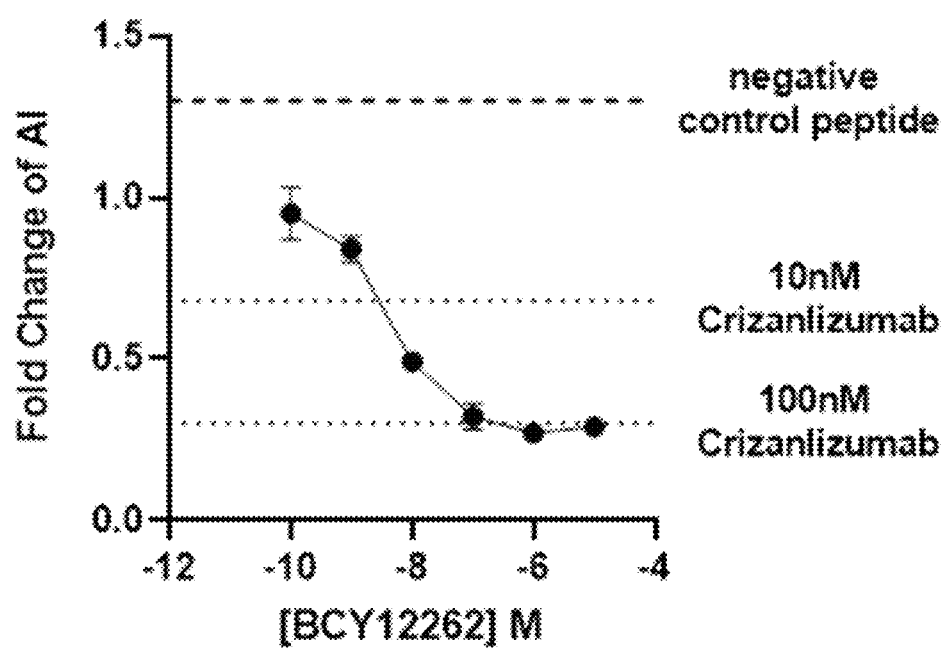
FIG. 2: Effect of BCY12262 on isolated white blood cell flow adhesion on P-selectin. Fold change of AI (adhesion index: cells/mm²) from baseline (no-drug control, not displayed on graph). Mean of 3 data points displayed with error bars denoting the standard deviation. Dashed lines represent the mean of the samples displayed.

The results of this analysis are shown in FIG. 2 where it can be seen that significant inhibition of white blood cell adhesion was observed for BCY12262 that compares well to the positive control antibody (crizanlizumab). BCY12262 showed a strong dose-response relationship with approximately 70 percent inhibition reached at higher doses (100 nM to 10 μM). Negative control peptide BCY17800 that does not bind to P-selectin showed no inhibition in the flow adhesion assay at 104.

The invention claimed is:

1. A peptide ligand specific for P-selectin comprising a polypeptide comprising at least three reactive groups, separated by at least two loop sequences, and a molecular scaffold which forms covalent bonds with the reactive groups of the polypeptide such that at least two polypeptide loops are formed on the molecular scaffold, wherein said peptide ligand comprises a motif WCDV, or a modified derivative thereof.

2. The peptide ligand as defined in claim 1, wherein said reactive groups comprise cysteine residues.

3. The peptide ligand as defined in claim 1, wherein said loop sequences comprise 4 or 6 amino acids.

4. The peptide ligand as defined in claim 1, wherein said loop sequences comprise three cysteine residues separated by two loop sequences the first of which consists of 4 amino acids and the second of which consists of 6 amino acids.

5. The peptide ligand as defined in claim 4, wherein said peptide ligand comprises an amino acid sequence of:

$C_i$-$X_1$-$X_2$-$X_3$-$X_4$-$C_{ii}$-D-V-$X_5$-$X_6$-$X_7$-$X_8$-$C_{iii}$ (SEQ ID NO: 1), wherein:
$X_1$ represents D or Y;
$X_2$ represents A or M;
$X_3$ represents D or E;
$X_4$ represents W, 1Nal or Trp (Me);
$X_5$ represents P or T;
$X_6$ represents S or D;
$X_7$ represents L or Y; and
$X_8$ represents P or G; and
wherein:
1Nal represents 1-naphthylalanine, Trp (Me) represents methyl-tryptophan, and $C_i$, $C_{ii}$ and $C_{iii}$ represent first, second and third cysteine residues, respectively, or a modified derivative, or a pharmaceutically acceptable salt thereof.

6. The peptide ligand as defined in claim 5, wherein $X_4$ represents W.

7. The peptide ligand as defined in claim 1, wherein the peptide ligand comprises an amino acid sequence selected from:

$C_i$DAD[1Nal]$C_{ii}$DVPSLP$C_{iii}$;  (SEQ ID NO: 2)

$C_i$DADW$C_{ii}$DVPSLP$C_{iii}$;  (SEQ ID NO: 3)

$C_i$YME[1Nal]$C_{ii}$DVTDYG$C_{iii}$;  (SEQ ID NO: 4)

-continued

C$_i$YME[Trp(Me)]CuDVTDYGC$_{iii}$; (SEQ ID NO: 5)
and

C$_i$YMEWC$_{ii}$DVTDYGC$_{iii}$; (SEQ ID NO: 6)

wherein C$_i$, C$_{ii}$ and C$_{iii}$ represent first, second and third cysteine residues, respectively, or a modified derivative, or a pharmaceutically acceptable salt thereof.

8. The peptide ligand as defined in claim 1, wherein the molecular scaffold is selected from: 1,1',1"-(1,3,5-triazinane-1,3,5-triyl) triprop-2-en-1-one (TATA), 1,1',1"-(1,4,7-triazonane-1,4,7-triyl) tris (2-chloroethan-1-one) (TCAZ), and 1,1',1"-(1,4,7-triazonane-1,4,7-triyl) tris (2-bromothan-1-one) (TBAZ).

9. The peptide ligand as defined in claim 1, wherein the peptide ligand is the free acid or a pharmaceutically acceptable salt selected from a sodium salt, a potassium salt, a calcium salt, and an ammonium salt.

10. A multimeric binding complex which comprises at least two peptide ligands, wherein at least one of said at least two peptide ligands is specific for P-selectin as defined in claim 1, wherein said at least two peptide ligands may be the same or different, and wherein each of said at least two peptide ligands comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

11. The multimeric binding complex as defined in claim 10, wherein each of the at least two peptide ligands is connected to a central hinge moiety by a spacer group.

12. The multimeric binding complex as defined in claim 10, which comprises a compound of formula (I):

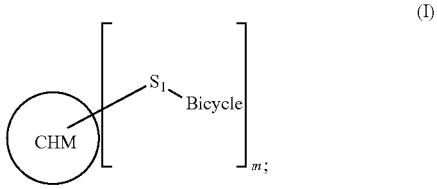

wherein CHM represents a central hinge moiety;
S$_1$ represents a spacer group;
Bicycle represents a peptide ligand specific for P-selectin comprising a polypeptide comprising at least three reactive groups, separated by at least two loop sequences, and a molecular scaffold which forms covalent bonds with the reactive groups of the polypeptide such that at least two polypeptide loops are formed on the molecular scaffold; and
m represents an integer selected from 2 to 10.

13. The multimeric binding complex as defined in claim 10, wherein said at least two peptide ligands are specific for the same target.

14. The multimeric binding complex as defined in claim 10, wherein the multimeric binding complex comprises at least two identical peptide ligands.

15. The multimeric binding complex as defined in claim 14, wherein the multimeric binding complex comprises two identical peptide ligands and is selected from: BCY5454, BCY5455, BCY5456, BCY5457, BCY12257, BCY12258, BCY19243, and BCY19240.

16. The multimeric binding complex as defined in claim 14, wherein the multimeric binding complex comprises three identical peptide ligands and is selected from: BCY5458, BCY5459, BCY5460, BCY5461, BCY12259, BCY12260, BCY19242, and BCY19239.

17. The multimeric binding complex as defined in claim 14, wherein the multimeric binding complex comprises four identical peptide ligands and is selected from: BCY5462, BCY5463, BCY5464, BCY5465, BCY12261, BCY12262, BCY11903, and BCY19238.

18. The multimeric binding complex as defined in claim 10, wherein the multimeric binding complex comprises at least two differing peptide ligands.

19. A drug conjugate comprising the peptide ligand as defined in claim 1 conjugated to one or more effector and/or functional groups.

20. A pharmaceutical composition comprising the peptide ligand as defined in claim 1 in combination with one or more pharmaceutically acceptable excipients.

21. The peptide ligand as defined in claim 7, wherein the peptide ligand comprises an amino acid sequence selected from:
A-(SEQ ID NO: 2)-A (herein referred to as BCY12027);
H$_2$N-A-(SEQ ID NO: 2)-A-[K (PYA)] (herein referred to as BCY12026);
A-(SEQ ID NO: 3)-A (herein referred to as BCY11648);
H$_2$N-A-(SEQ ID NO: 3)-A-[K (PYA)] (herein referred to as BCY12025);
Ac-A-(SEQ ID NO: 4)-A (herein referred to as BCY11279);
A-(SEQ ID NO: 4)-A-[K (PYA)] (herein referred to as BCY11890);
Ac-A-(SEQ ID NO: 5)-A (herein referred to as BCY11281);
Ac-(SEQ ID NO: 6) (herein referred to as BCY9717);
A-(SEQ ID NO: 6)-A (herein referred to as BCY10194);
A-(SEQ ID NO: 6)-A-[K (PYA)] (herein referred to as BCY18041);
[PYA]-A-(SEQ ID NO: 6)-A-NH$_2$ (herein referred to as BCY10910); and
Ac-A-(SEQ ID NO: 6)-[K (PYA)]-NH$_2$ (herein referred to as BCY10911).

22. The peptide ligand as defined in claim 7, wherein the peptide ligand comprises an amino acid sequence H$_2$N-A-(SEQ ID NO: 2)-A-[K (PYA)] (herein referred to as BCY12026).

23. A pharmaceutical composition comprising the multimeric binding complex as defined in claim 11 in combination with one or more pharmaceutically acceptable excipients.

* * * * *